(12) United States Patent
Stuurman

(10) Patent No.: US 8,716,550 B2
(45) Date of Patent: May 6, 2014

(54) METHOD FOR THE SELECTION OF PLANTS WITH SPECIFIC MUTATIONS

(75) Inventor: Jeroen Stuurman, Oosterbeek (NL)

(73) Assignee: Keygene N.V., Wageningen (NL)

( * ) Notice: Subject to any disclaimer, the term of this patent is extended or adjusted under 35 U.S.C. 154(b) by 654 days.

(21) Appl. No.: 12/679,565

(22) PCT Filed: Sep. 24, 2008

(86) PCT No.: PCT/NL2008/000209
§ 371 (c)(1),
(2), (4) Date: Apr. 9, 2010

(87) PCT Pub. No.: WO2009/041810
PCT Pub. Date: Apr. 2, 2009

(65) Prior Publication Data
US 2010/0212043 A1      Aug. 19, 2010

Related U.S. Application Data

(60) Provisional application No. 60/974,612, filed on Sep. 24, 2007.

(51) Int. Cl.
*A01H 1/06* (2006.01)
(52) U.S. Cl.
USPC ....................................................... 800/270
(58) Field of Classification Search
None
See application file for complete search history.

(56) References Cited

U.S. PATENT DOCUMENTS 6,730,832 B1    5/2004   Dominguez et al.

FOREIGN PATENT DOCUMENTS

WO       WO 99/65292        12/1999
WO       WO 2007/037678 A2   4/2007

OTHER PUBLICATIONS

De Haro et al (Crop Science 41: 281-282, 2001).*
Till et al (BMC Plant Biology 4: 12, 2004).*
McCallum et al (Plant Physiology 123: 439-442, 2000).*
Zamir (Nature Reviews 2:983-989, Dec. 2001).*
The International Search Report received in the corresponding application PCT/NL2008/000209, dated Jan. 27, 2009.
Till, et al., "Large-Scale Discovery of Induced Point Mutations with High-Throughput Tilling", *Genome Research*, 2003, vol. 13, pp. 524-530.
Vandenbussche, et al., "Toward the Analysis of the Petunia MADS Box Gene Family by Reverse and Forward Transposon Insertion Mutagenesis Approaches: B, C, and D Floral Organ Identity Functions require *SEPALLATA*-Like MADS Box Genes in petunia", *The Plant Cell*, vol. 15, pp. 2680-5693.

* cited by examiner

*Primary Examiner* — Shubo (Joe) Zhou
*Assistant Examiner* — Keith Robinson
(74) *Attorney, Agent, or Firm* — Foley & Lardner LLP

(57) ABSTRACT

The present invention relates to a method for the provision of mutagenised populations by the introduction of mutations by chemically and or physically mutagens in a selected region of the genome of a plant and the subsequent selection of inheritable mutations by analysis of at least one section of a mutagenised primary M1 plant for the presence of a mutation in the region of interest using high throughput sequencing.

21 Claims, 11 Drawing Sheets

FIG 1
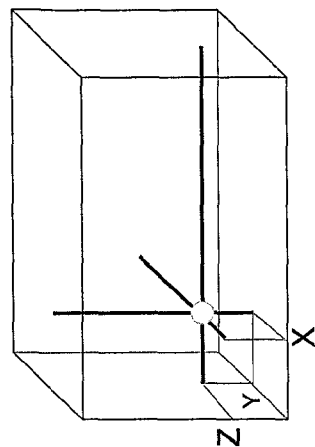
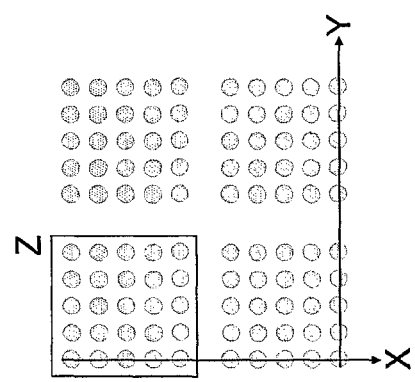
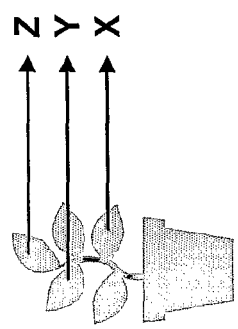

Fig 3

```
1                                                              60
f1_(m1xw5)_col5
ATGAGATGAAGCACTCAAATGATGCACTTCATGTGGTAATGTTCCCATTTTTTGCTTTTG
m1_col10
ATGAGATGAAGCACTCAAATGATGCACTTCATGTGGTAATGTTCCCATTTTTTGCTTTTG
m2_col3
GAGATGAAGCACTCAAATGATGCACTTCATGTGGTAATGTTCCCATTTTTTGCTTTTG
m4_col16
ATGAGATGAAGCACTCAAATGATGCACTTCATGTGGTAATGTTCCCATTTTTTGCTTTTG
m16_col4
ATGAGATGAAGCACTCAAATGATGCACTTCATGTGGTAATGTTCCCATTTTTTGCTTTTG
m17_col11
ATGAGATGAAGCACTCAAATGATGCACTTCATGTGGTAATGTTCCCATTTTTTGCTTTTG
m20_col19
ATGAGATGAAGCACTCAAATGATGCACTTCATGTGGTAATGTTCCCATTTTTTGCTTTTG 61                                                             120
f1_(m1xw5)_col5
GCCATATTAGTCCATTTGTGCAGCTTGCTAACAAGTTGTCCTCTTATGGTGTCAAAGTTT
m1_col10
GCCATATTAGTCCATTTGTGCAGCTTGCTAACAAGTTGTCCTCTTATGGTGTCAAAGTTT
m2_col3
GCCATATTAGTCCATTTGTGCAGCTTGCTAACAAGTTGTCCTCTTATGGTGTCAAAGTTT
m4_col16
GCCATATTAGTCCATTTGTGCAGCTTGCTAACAAGTTGTCCTCTTATGGTGTCAAAGTTT
m16_col4
GCCATATTAGTCCATTTGTGCAGCTTGCTAACAAGTTGTCCTCTTATGGTGTCAAAGTTT
m17_col11
GCCATATTAGTCCATTTGTGCAGCTTGCTAACAAGTTGTCCTCTTATGGTGTCAAAGTTT
m20_col19
GCCATATTAGTCCATTTGTGCAGCTTGCTAACAAGTTGTCCTCTTATGGTGTCAAAGTTT 121                                                            180
f1_(m1xw5)_col5
CTTTCTTCACAGCATCTGGCAATGCCAGCAGAGTCAAATCTATGTTAAATTCTGCTCCCA
m1_col10
CTTTCTTCACAGCATCTGGCAATGCCAGCAGAGTCAAATCTATGTTAAATTCTGCTCCCA
m2_col3
CTTTCTTCACAGCATCTGGCAATGCCAGCAGAGTCAAATCTATGTTAAATTCTGCTCCCA
m4_col16
CTTTCTTCACAGCATCTGGCAATGCCAGCAGAGTCAAATCTATGTTAAATTCTGCTCCCA
m16_col4
CTTTCTTCACAGCATCTGGCAATGCCAGCAGAGTCAAATCTATGTTAAATTCTGCTCCCA
m17_col11
CTTTCTTCACAGCATCTGGCAATGCCAGCAGAGTCAAATCTATGTTAAATTCTGCTCCCA
m20_col19
CTTTCTTCACAGCATCTGGCAATGCCAGCAGAGTCAAATCTATGTTAAATTCTGCTCCCA 181                                                            240
f1_(m1xw5)_col5
CTACTCATATAGTCCCTCTCACACTTCCTCATGTTGAAGGTCTACCTCCTGGTGCAGAAA
m1_col10
CTACTCATATAGTCCCTCTCACACTTCCTCATGTTGAAGGTCTACCTCCTGGTGCAGAAA
m2_col3
CTACTCATATAGTCCCTCTCACACTTCCTCATGTTGAAGGTCTACCTCCTGGTGCAGAAA
m4_col16
CTACTCATATAGTCCCTCTCACACTTCCTCATGTTGAAGGTCTACCTCCTGGTGCAGAAA
```

Fig 3 cont'd m16_col4
CTACTCATATAGTCCCTCTCACACTTCCTCATGTTGAAGGTCTACCTCCTGGTGCAGAAA
m17_col11
CTACTCATATAGTCCCTCTCACACTTCCTCATGTTGAAGGTCTACCTCCTGGTGCAGAAA
m20_col19
CTACTCATATAGTCCCTCTCACACTTCCTCATGTTGAAGGTCTACCTCCTGGTGCAGAAA 241                                                        300
f1_(m1xw5)_col5
GTACTGCAGAATTGACACCAGCTAGTGCTGAGCTTCTCAAGGTTGCTTTAGACCTAATGC
m1_col10
GTACTGCAGAATTGACACCAGCTAGTGCTGAGCTTCTCAAGGTTGCTTTAGACCTAATGC
m2_col3
GTACTGCAGAATTGACACCAGCTAGTGCTGAGCTTCTCAAGGTTGCTTTAGACCTAATGC
m4_col16
GTACTGCAGAATTGACACCAGCTAGTGCTGAGCTTCTCAAGGTTGCTTTAGACCTAATGC
m16_col4
GTACTGCAGAATTGACACCAGCTAGTGCTGAGCTTCTCAAGGTTGCTTTAGACCTAATGC
m17_col11
GTACTGCAGAATTGACACCAGCTAGTGCTGAGCTTCTCAAGGTTGCTTTAGACCTAATGC
m20_col19
GTACTGCAGAATTGACACCAGCTAGTGCTGAGCTTCTCAAGGTTGCTTTAGACCTAATGC 301                                                        360
f1_(m1xw5)_col5
AACCACAAATCAAGACTTTACTTTCCCATCTCAAACCCCATTTTGTTCTCTTTGATTTTG
m1_col10
AACCACAAATCAAGACTTTACTTTCCCATCTCAAACCCCATTTTGTTCTCTTTGATTTTG
m2_col3
AACCACAAATCAAGACTTTACTTTCCCATCTCAAACCCCATTTTGTTCTCTTTGATTTTG
m4_col16
AACCACAAATCAAGACTTTACTTTCCCATCTCAAACCCCATTTTGTTCTCTTTGATTTTG
m16_col4
AACCACAAATCAAGACTTTACTTTCCCATCTCAAACCCCATTTTGTTCTCTTTGATTTTG
m17_col11
AACCACAAATCAAGACTTTACTTTCCCATCTCAAACCCCATTTTGTTCTCTTTGATTTTG
m20_col19
AACCACAAATCAAGACTTTACTTTCCCATCTCAAACCCCATTTTGTTCTCTTTGATTTTG 361                                                        420
f1_(m1xw5)_col5
CTCAAGAATGGCTTCCTAAAATGGCCAATGGATTGGGTATCAAGACTGTTTATTACTCTG
m1_col10
CTCAAGAATGGCTTCCTAAAATGGCCAATGGATTGGGTATCAAGACTGTTTATTACTCTG
m2_col3
CTCAAGAATGGCTTCCTAAAATGGCCAATGGATTGGGTATCAAGACTGTTTATTACTCTG
m4_col16
CTCAAGAATGGCTTCCTAAAATGGCCAATGGATTGGGTATCAAGACTGTTTATTACTCTG
m16_col4
CTCAAGAATGGCTTCCTAAAATGGCCAATGGATTGGGTATCAAGACTGTTTATTACTCTG
m17_col11
CTCAAGAATGGCTTCCTAAAATGGCCAATGGATTGGGTATCAAGACTGTTTATTACTCTG
m20_col19
CTCAAGAATGGCTTCCTAAAATGGCCAATGGATTGGGTATCAAGACTGTTTATTACTCTG
421                                                        480

Fig 3 cont'd f1_(m1xw5)_col5
TTGTTGTTGCACTTTCCACTGCTTTTCTTACTTGTCCTGCTA▓AGTTCTTGAACCCAAAA
m1_col10
TTGTTGTTGCACTTTCCACTGCTTTTCTTACTTGTCCTGCTA▓AGTTCTTGAACCCAAAA
m2_col3
TTGTTGTTGCACTTTCCACTGCTTTTCTTACTTGTCCTGCTA▓AGTTCTTGAACCCAAAA
m4_col16
TTGTTGTTGCACTTTCCACTGCTTTTCTTACTTGTCCTGCTA▓AGTTCTTGAACCCAAAA
m16_col4
TTGTTGTTGCACTTTCCACTGCTTTTCTTACTTGTCCTGCTA▓AGTTCTTGAACCCAAAA
m17_col11
TTGTTGTTGCACTTTCCACTGCTTTTCTTACTTGTCCTGCTA▓AGTTCTTGAACCCAAAA
m20_col19
TTGTTGTTGCACTTTCCACTGCTTTTCTTACTTGTCCTGCTAAAGTTCTTGAACCCAAAA 481                                                        540
f1_(m1xw5)_col5
AGTATCCAAGTCTCGAAGACATGAAGAAACCTCCACTTGGGTTTCCTCAGACCTCTGTTA
m1_col10
AGTATCCAAGTCTCGAAGACATGAAGAAACCTCCACTTGGGTTTCCTCAGACCTCTGTTA
m2_col3
AGTATCCAAGTCTCGAAGACATGAAGAAACCTCCACTTGGGTTTCCTCAGACCTCTGTTA
m4_col16
AGTATCCAAGTCTCGAAGACATGAAGAAACCTCCACTTGGGTTTCCTCAGACCTCTGTTA
m16_col4
AGTATCCAAGTCTCGAAGACATGAAGAAACCTCCACTTGGGTTTCCTCAGACCTCTGTTA
m17_col11
AGTATCCAAGTCTCGAAGACATGAAGAAACCTCCACTTGGGTTTCCTCAGACCTCTGTTA
m20_col19
AGTATCCAAGTCTCGAAGACATGAAGAAACCTCCACTTGGGTTTCCTCAGACCTCTGTTA 541                                                        600
f1_(m1xw5)_col5
CCTCAGTCAGAACCTTTGAGGCTAGAGATTTTCTATATGTTTTCAAGAGTTTCCATAATG
m1_col10
CCTCAGTCAGAACCTTTGAGGCTAGAGATTTTCTATATGTTTTCAAGAGTTTCCATAATG
m2_col3
CCTCAGTCAGAACCTTTGAGGCTAGAGATTTTCTATATGTTTTCAAGAGTTTCCATAATG
m4_col16
CCTCAGTCAGAACCTTTGAGGCTAGAGATTTTCTATATGTTTTCAAGAGTTTCCATAATG
m16_col4
CCTCAGTCAGAACCTTTGAGGCTAGAGATTTTCTATATGTTTTCAAGAGTTTCCATAATG
m17_col11
CCTCAGTCAGAACCTTTGAGGCTAGAGATTTTCTATATGTTTTCAAGAGTTTCCATAATG
m20_col19
CCTCAGTCAGAACCTTTGAGGCTAGAGATTTTCTATATGTTTTCAAGAGTTTCCATAATG 601                                                        660
f1_(m1xw5)_col5
GTCCTACTTTATATGAC▓GTATACAGTCAGGACTCAGGGGGTGCTCAGCTATACTAGCAA
m1_col10
GTCCTACTTTATATGAC▓GTATACAGTCAGGACTCAGGGGGTGCTCAGCTATACTAGCAA
m2_col3
GTCCTACTTTATATGAC▓GTATACAGTCAGGACTCAGGGGGTGCTCAGCTATACTAGCAA
m4_col16
GTCCTACTTTATATGAC▓GTATACAGTCAGGACTCAGGGGGTGCTCAGCTATACTAGCAA

Fig 3 cont'd m16_col4
GTCCTACTTTATATGACAGTATACAGTCAGGACTCAGGGGGTGCTCAGCTATACTAGCAA
m17_col11
GTCCTACTTTATATGAC☒GTATACAGTCAGGACTCAGGGGGTGCTCAGCTATACTAGCAA
m20_col19
GTCCTACTTTATATGAC☒GTATACAGTCAGGACTCAGGGGGTGCTCAGCTATACTAGCAA 661                                                          720
f1_(m1xw5)_col5
AAACTTGTTCACAAATGGAGGGTCCTTATATAAAATACGTAGAAGCACAATTCAATAAAC
m1_col10
AAACTTGTTCACAAATGGAGGGTCCTTATATAAAATACGTAGAAGCACAATTCAATAAAC
m2_col3
AAACTTGTTCACAAATGGAGGGTCCTTATATAAAATACGTAGAAGCACAATTCAATAAAC
m4_col16
AAACTTGTTCACAAATGGAGGGTCCTTATATAAAATACGTAGAAGCACAATTCAATAAAC
m16_col4
AAACTTGTTCACAAATGGAGGGTCCTTATATAAAATACGTAGAAGCACAATTCAATAAAC
m17_col11
AAACTTGTTCACAAATGGAGGGTCCTTATATAAAATACGTAGAAGCACAATTCAATAAAC
m20_col19
AAACTTGTTCACAAATGGAGGGTCCTTATATAAAATACGTAGAAGCACAATTCAATAAAC 721                                                          780
f1_(m1xw5)_col5
CTGTTTTTCTAATC☒GACCCGTAGTTCCGGACCCGCCTTCGGGTAAATTGGAAGAGAAAT
m1_col10
CTGTTTTTCTAATC☒GACCCGTAGTTCCGGACCCGCCTTCGGGTAAATTGGAAGAGAAAT
m2_col3
CTGTTTTTCTAATC☒GACCCGTAGTTCCGGACCCGCCTTCGGGTAAATTGGAAGAGAAAT
m4_col16
CTGTTTTTCTAATCAGACCCGTAGTTCCGGACCCGCCTTCGGGTAAATTGGAAGAGAAAT
m16_col4
CTGTTTTTCTAATC☒GACCCGTAGTTCCGGACCCGCCTTCGGGTAAATTGGAAGAGAAAT
m17_col11
CTGTTTTTCTAATC☒GACCCGTAGTTCCGGACCCGCCTTCGGGTAAATTGGAAGAGAAAT
m20_col19
CTGTTTTTCTAATC☒GACCCGTAGTTCCGGACCCGCCTTCGGGTAAATTGGAAGAGAAAT 781                                                          840
f1_(m1xw5)_col5
GGGCTACTTGGTTAAACAAGTTTGAAGGTGGAACAGTTATTTACTGTTCTTTTGGAAGTG
m1_col10
GGGCTACTTGGTTAAACAAGTTTGAAGGTGGAACAGTTATTTACTGTTCTTTTGGAAGTG
m2_col3
GGGCTACTTGGTTAAACAAGTTTGAAGGTGGAACAGTTATTTACTGTTCTTTTGGAAGTG
m4_col16
GGGCTACTTGGTTAAACAAGTTTGAAGGTGGAACAGTTATTTACTGTTCTTTTGGAAGTG
m16_col4
GGGCTACTTGGTTAAACAAGTTTGAAGGTGGAACAGTTATTTACTGTTCTTTTGGAAGTG
m17_col11
GGGCTACTTGGTTAAACAAGTTTGAAGGTGGAACAGTTATTTACTGTTCTTTTGGAAGTG
m20_col19
GGGCTACTTGGTTAAACAAGTTTGAAGGTGGAACAGTTATTTACTGTTCTTTTGGAAGTG

Fig 3 cont'd

```
841                                                          900
f1_(m1xw5)_col5
AAACTTTCTTGACTGATGATCAGGTCAAAGAACTGGCTTTAGGTTTGGAACAGACAGGGC
m1_col10
AAACTTTCTTGACTGATGATCAGGTCAAAGAACTGGCTTTAGGTTTGGAACAGACAGGGC
m2_col3
AAACTTTCTTGACTGATGATCAGGTCAAAGAACTGGCTTTAGGTTTGGAACAGACAGGGC
m4_col16
AAACTTTCTTGACTGATGATCAGGTCAAAGAACTGGCTTTAGGTTTGGAACAGACAGGGC
m16_col4
AAACTTTCTTGACTGATGATCAGGTCAAAGAACTGGCTTTAGGTTTGGAACAGACAGGGC
m17_col11
AAACTTTCTTGACTGATGATCAGGTCAAAGAACTGGCTTTAGGTTTGGAACAGACAGGGC
m20_col19
AAACTTTCTTGACTGATGATCAGGTCAAAGAACTGGCTTTAGGTTTGGAACAGACAGGGC 901                                                          960
f1_(m1xw5)_col5
TTCCTTTCTTTCTTGTCTTAAATTTTCCTGCAAATGTTGATGTTTCAGCGGAGCTAAACC
m1_col10
TTCCTTTCTTTCTTGTCTTAAATTTTCCTGCAAATGTTGATGTTTCAGCGGAGCTAAACC
m2_col3
TTCCTTTCTTTCTTGTCTTAAATTTTCCTGCAAATGTTGATGTTTCAGCGGAGCTAAACC
m4_col16
TTCCTTTCTTTCTTGTCTTAAATTTTCCTGCAAATGTTGATGTTTCAGCGGAGCTAAACC
m16_col4
TTCCTTTCTTTCTTGTCTTAAATTTTCCTGCAAATGTTGATGTTTCAGCGGAGCTAAACC
m17_col11
TTCCTTTCTTTCTTGTCTTAAATTTTCCTGCAAATGTTGATGTTTCAGCGGAGCTAAACC
m20_col19
TTCCTTTCTTTCTTGTCTTAAATTTTCCTGCAAATGTTGATGTTTCAGCGGAGCTAAACC 961                                                          1020
f1_(m1xw5)_col5
GAGCTTTACCTGAAGGGTTTCTGGAAAGAGTGAAAGACAAGGGGATTATTCATTCAGGTT
m1_col10
GAGCTTTACCTGAAGGGTTTCTGGAAAGAGTGAAAGACAAGGGGATTATTCATTCAGGTT
m2_col3
GAGCTTTACCTGAAGGGTTTCTGGAAAGAGTGAAAGACAAGGGGATTATTCATTCAGGTT
m4_col16
GAGCTTTACCTGAAGGGTTTCTGGAAAGAGTGAAAGACAAGGGGATTATTCATTCAGGTT
m16_col4
GAGCTTTACCTGAAGGGTTTCTGGAAAGAGTGAAAGACAAGGGGATTATTCATTCAGGTT
m17_col11
GAGCTTTACCTGAAGGGTTTCTGGAAAGAGTGAAAGACAAGGGGATTATTCATTCAGGTT
m20_col19
GAGCTTTACCTGAAGGGTTTCTGGAAAGAGTGAAAGACAAGGGGATTATTCATTCAGGTT 1021                                                         1080
f1_(m1xw5)_col5
GGGTGCAACAGCAGAATATATTAGCTCATTCTAGTGTAGGTTGTTATGTATGTCATGCAG
m1_col10
GGGTGCAACAGCAGAATATATTAGCTCATTCTAGTGTAGGTTGTTATGTATGTCATGCAG
m2_col3
GGGTGCAACAGCAGAATATATTAGCTCATTCTAGTGTAGGTTGTTATGTATGTCATGCAG
m4_col16
GGGTGCAACAGCAGAATATATTAGCTCATTCTAGTGTAGGTTGTTATGTATGTCATGCAG
```

Fig 3 cont'd

```
m16_col4
GGGTGCAACAGCAGAATATATTAGCTCATTCTAGTGTAGGTTGTTATGTATGTCATGCAG
m17_col11
GGGTGCAACAGCAGAATATATTAGCTCATTCTAGTGTAGGTTGTTATGTATGTCATGCAG
m20_col19
GGGTGCAACAGCAGAATATATTAGCTCATTCTAGTGTAGGTTGTTATGTATGTCATGCAG 1081                                                      1140
f1_(m1xw5)_col5
GGTTTA TTCAGTTATA AGGCACTGGTGAATGACTGTCAAGTAGTTATGTTGCCCCAGA
m1_col10
GGTTTA TTCAGTTATAAAGGCACTGGTGAATGACTGTCAAGTAGTTATGTTGCCCCAGA
m2_col3
GGTTTAATTCAGTTATA AGGCACTGGTGAATGACTGTCAAGTAGTTATGTTGCCCCAGA
m4_col16
GGTTTA TTCAGTTATA AGGCACTGGTGAATGACTGTCAAGTAGTTATGTTGCCCCAGA
m16_col4
GGTTTA TTCAGTTATA AGGCACTGGTGAATGACTGTCAAGTAGTTATGTTGCCCCAGA
m17_col11
GGTTTA TTCAGTTATA AGGCACTGGTGAATGACTGTCAAGTAGTTATGTTGCCCCAGA
m20_col19
GGTTTA TTCAGTTATA AGGCACTGGTGAATGACTGTCAAGTAGTTATGTTGCCCCAGA 1141                                                      1200
f1_(m1xw5)_col5
AAGRTGACC GATTTTGAATGCAAAGCTGGTGAGDTHTGGTGATATGGAAGCTGGGGTGG
m1_col10
AAGGTGACC GATTTTGAATGCAAAGCTGGTGAGDTHTGGTGATATGGAAGCTGGGGTGG
m2_col3
AAGGTGACC GATTTTGAATGCAAAGCTGGTGAGDTHTGGTGATATGGAAGCTGGGGTGG
m4_col16
AAGGTGACC GATTTTGAATGCAAAGCTGGTGAGDTHTGGTGATATGGAAGCTGGGGTGG
m16_col4
AAGGTGACC GATTTTGAATGCAAAGCTGGTGAGDTHTGGTGATATGGAAGCTGGGGTGG
m17_col11
AAGGTGACCTGATTTTGAATGCAAAGCTGGTGAGDTHTGGTGATATGGAAGCTGGGGTGG
m20_col19
AAGGTGACC GATTTTGAATGCAAAGCTGGTGAGDTHTGGTGATATGGAAGCTGGGGTGG 1201                                                      1260
f1_(m1xw5)_col5
AGATTAATAGGAGGGATGAAGATGGTTATTTTGGTAAAGAAGATATTAAGGAAGCTGTGG
m1_col10
AGATTAATAGGAGGGATGAAGATGGTTATTTTGGTAAAGAAGATATTAAGGAAGCTGTGG
m2_col3
AGATTAATAGGAGGGATGAAGATGGTTATTTTGGTAAAGAAGATATTAAGGAAGCTGTGG
m4_col16
AGATTAATAGGAGGGATGAAGATGGTTATTTTGGTAAAGAAGATATTAAGGAAGCTGTGG
m16_col4
AGATTAATAGGAGGGATGAAGATGGTTATTTTGGTAAAGAAGATATTAAGGAAGCTGTGG
m17_col11
AGATTAATAGGAGGGATGAAGATGGTTATTTTGGTAAAGAAGATATTAAGGAAGCTGTGG
m20_col19
AGATTAATAGGAGGGATGAAGATGGTTATTTTGGTAAAGAAGATATTAAGGAAGCTGTGG 1261                                                      1320
```

Fig 3 cont'd

```
f1_(m1xw5)_col5
AAAAGGTGATGGTGGATGTTGAAAAGGASCCAGGTAAATTAATTAGGGAAAATCAGAAGA
m1_col10
AAAAGGTGATGGTGGATGTTGAAAAGGAGCCAGGTAAATTAATTAGGGAAAATCAGAAGA
m2_col3
AAAAGGTGATGGTGGATGTTGAAAAGGAGCCAGGTAAATTAATTAGGGAAAATCAGAAGA
m4_col16
AAAAGGTGATGGTGGATGTTGAAAAGGAGCCAGGTAAATTAATTAGGGAAAATCAGAAGA
m16_col4
AAAAGGTGATGGTGGATGTTGAAAAGGAGCCAGGTAAATTAATTAGGGAAAATCAGAAGA
m17_col11
AAAAGGTGATGGTGGATGTTGAAAAGGAGCCAGGTAAATTAATTAGGGAAAATCAGAAGA
m20_col19
AAAAGGTGATGGTGGATGTTGAAAAGGAGCCAGGTAAATTAATTAGGGAAAATCAGAAGA 1321                                                      1380
f1_(m1xw5)_col5
AATGGAAGGAGTTTCTGTTGAACAAGGATATCCAGTCCAAATATATTGGGAATTTAGTTA
m1_col10
AATGGAAGGAGTTTCTGTTGAACAAGGATATCCAGTCCAAATATATTGGGAATTTAGTTA
m2_col3
AATGGAAGGAGTTTCTGTTGAACAAGGATATCCAGTCCAAATATATTGGGAATTTAGTTA
m4_col16
AATGGAAGGAGTTTCTGTTGAACAAGGATATCCAGTCCAAATATATTGGGAATTTAGTTA
m16_col4
AATGGAAGGAGTTTCTGTTGAACAAGGATATCCAGTCCAAATATATTGGGAATTTAGTTA
m17_col11
AATGGAAGGAGTTTCTGTTGAACAAGGATATCCAGTCCAAATATATTGGGAATTTAGTTA
m20_col19
AATGGAAGGAGTTTCTGTTGAACAAGGATATCCAGTCCAAATATATTGGGAATTTAGTTA 1381        1397
f1_(m1xw5)_col5         ATGAAATGACAGCCAT-
m1_col10                ATGAAATGACAGCCATG
m2_col3                 ATGAAATGACAGCCA--
m4_col16                ATGAAATGACAGCCAT-
m16_col4                ATGAAATGACAGCCA--
m17_col11               ATGAAATGACAGCCATG
m20_col19               ATGAAATGACAGCCAT-
```

FIG 4

TCATTCAGGTTGGGTGCAACAGCAGAATATATTAGCTCATTCTAGTGTAGGTT

M2 (G->A)
GTTATGTATGTCATGCAGGGTTTAGTTCAGTTATAGAGGCACTGGTGAATGAC

M17 (A->T)
TGTCAAGTAGTTATGTTGCCCCAGAAAGGTGACCAGATTTTGAATGCAAAGC

TGGTGAGTGGTGATATGGAAGCTGGGGTGGA

FIG 5
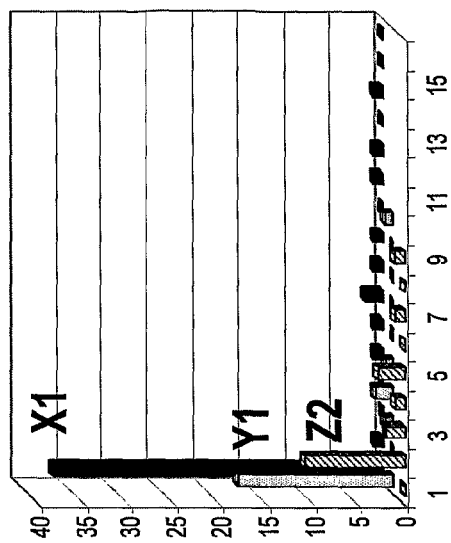
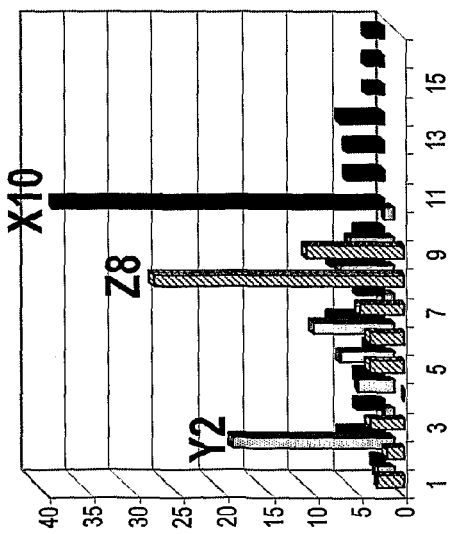

METHOD FOR THE SELECTION OF PLANTS WITH SPECIFIC MUTATIONS

CROSS-REFERENCE TO RELATED PATENT APPLICATIONS

This application is the U.S. National Phase of PCT/NL2008/000209, filed Sep. 24, 2008, which claims priority from U.S. Provisional Application No. 60/974,612, filed Sep. 24, 2007, all of which are incorporated herein by reference in entirety.

The present invention relates to a method for the selection of plants with specific mutations. In particular, the method relates to a method for the selection of plants that have a mutation in a desired genomic area that may lead to improved genetic variation and improved phenotypes.

Breeding of elite germplasm is a time consuming and costly process. Once elite lines are established, breeders will avoid conventional crossing and selection methodologies with non-adapted germplasm, as this will disintegrate the optimal genetic make up of the lines. Conversely, there is an increasing interest in creating genetic variation in specific breeding lines through the use of mutation induction techniques. The impact of induced mutation on crop improvement is reflected in the 2316 officially registered varieties (IAEA's database on officially registered mutant varieties) carrying novel induced variation. Moreover, about three-quarters of these are direct mutant varieties derived from treatment with gamma rays, thus highlighting the importance of the creation of genetic variety through mutation. All this translates into a tremendous economic impact on agriculture and food production that is currently valued in billions of dollars and millions of cultivated hectares. However, while the agronomic potential of induced mutation is well understood, there are still problems to solve with respect to the use of mutations.

Mutagenic agents can be classified into three categories: physical (e.g., gamma rays), chemical (e.g., ethyl methane sulphonate, EMS) and transposable elements (such as transposons, retrotransposons, T-DNA, retroviruses). At present, limited data are available on the scope of genetic effects induced at the molecular level in plants and on the specificity and relative efficiency of these different categories of agents and the mutations they cause. These effects involve DNA damage, which results in base pair changes (single/simple nucleotide polymorphisms, SNPs), small insertions and deletions (indels) and chromosomal rearrangements. Even less is known about how induced mutation interact with epigenetic processes, such as methylation, activation of retro-elements, and perturbation of higher order DNA structure.

While breeders have been using mutation induction to broaden the genetic base of germplasm, and have used the mutant lines directly as new varieties or as sources of new variation in cross-breeding programmes, knowledge of the precise nature of the induced mutations was not necessary. Intuitively a conservative level of small base pair rearrangement and deletion was considered to be ideal. Nowadays, the use of mutation techniques has expanded beyond applications in breeding to gene discovery and reverse genetics. These new high-throughput applications require specific classes of mutations that are induced with high efficiency over entire crop plant genomes, and consequently knowledge of the precise nature of induced mutation is becoming an issue.

Classic high-throughput gene discovery methods depend heavily on insertional 'knockout' lines, the now classical 'gene machines', and deletion 'knockout' libraries. Insertional mutagenesis involves inducing activity of transposition of known transposable elements to produce series of lines in which, in theory, every gene in the genome will have been inactivated by the transposon insertion. These lines can be used to identify genes that cause particular phenotypes or, conversely, can be used to identify gene function by searching for a phenotype associated with the inactivation of a particular known gene. However, insertional mutants have the drawback that gene function is heavily perturbed, usually presenting full gene knockout In many cases, mutations are desired that modify a gene rather than eliminate it. In comparison to insertional mutagenesis, conventional mutation induction (particularly chemical agents such as EMS) provides the advantage of inducing point mutations and therefore a wide range of potential allelic variation.

A relative novel and important reverse genetics approach is 'targeting induced local lesions in genomes' (TILLING). Here, large numbers of small changes, either DNA base pair substitutions or small deletions spanning no more than a few base pairs, are induced in a series of lines. In these lines gene function can be ascertained by associating a phenotype with changes in a particular gene and novel alleles of known genes can be generated.

Over the coming years, new technologies such as these will have increasing impact in practical plant breeding. In order to tailor the mutation process, there will be a need for techniques that makes the selection of mutants that contain a mutation in a desired section of the genome easier. Furthermore there will be a need for techniques to select from a large number of mutants, those mutants in which mutations have been introduced in a stable form, i.e. can be used in breeding and distributed over genomes. In the past, this has not been possible because of lack of analytical tools and methodologies. Today, high-throughput DNA sequencing methods, comprising inter alia parallel sequencing methods, single molecule sequencing provide part of the above described missing links. A good example is for instance provided in applicants' technology and co-pending application depicted as Keypoints (WO2007037678).

However, the use of Keypoints to select induced mutations in specific genes may in practice be restricted to specially made mutagenised populations that are stored as M2 or even later generation inbred populations. At least one selfing of primary mutagenised M1 seed is in practice deemed necessary to eliminate somatic chimerism prior to DNA analysis. Because the investment in time and resources for construction and propagation of such a mutagenised population is considerable, they are scarce and do typically not comprise a significant portion of the elite germplasm of a crop of a breeder. For the practical use of mutagenised populations in the improvement of elite breeding material, this is a serious drawback. There is a need, therefore, to invent methods that allow mutagenesis and mutant selection in any breeding line, and in any stage or pedigree in a breeding program.

The present inventor has now found a solution to the above problems. The solution is based on the insight that primary mutagenised seeds give rise to chimeric plants, and that sector analysis can be used to specifically select heritable mutations. Only those mutations that occur in the embryonic apical stem cells will be incorporated in the entire body of the plant and will ultimately be transmitted to progeny. Non-stem cell mutations will generally not occupy a major portion of the different parts of the plant, such as the first series of true leaves or flowers in young plantlets, and generally will not extend into the germline. This insight is exploited in the present invention to screen for heritable mutations in any M1 population of plants, directly after seed mutagenesis.

The method uses a specific multidimensional (more than 2) gridding strategy which pools different parts of the plants, such as the first true leaves in the first coordinate (x) of a multidimensional matrix, the second true leaves in the second coordinate (y), and, in the case of 3D pooling, the third true leaves in the third coordinate (z) (see figure). Instead of the true leaves one may also use the flowers or other parts (e.g. pollen) of the plant. Mutations detected in all three coordinates after KeyPoint (Tilling technology employing high throughput sequencing technology for the detection and identification of mutations instead of enzymes such as Cel1) analysis are considered to have originated in the stem cells, because they are consistently present in all consecutive leaves or other organs. Mutations detected in just one or two coordinates and lacking from a third are somatic sectors.

The present invention provides for the sampling and sequencing of mutagenised populations in limited time. The individual mutant plants can be selected from a population of any desired size, and propagated with a large chance of carrying a specific heritable mutation. The rest of the population can be discarded. The advantage of this approach is that specific mutations can be made in different crops and their elite line(s), depending on actual needs. Also, long generation plants ((fruit) trees, grapes, etc) become amenable, because mutant selection only requires seed to grow individual mutant plants, and no progeny or generation times.

In a first aspect, the present invention relates to a method for the introduction and selection of a specific mutation in plants, comprising the steps of:
(a) provide a plurality of mutagenised seeds;
(b) sow the mutagenised seeds in a N-dimensional grid, wherein N≥1, preferably 2, more preferably 3;
(c) grow plants (or seedlings) from the seeds;
(d) sample DNA-containing material from one section of the plant;
(e) pool the DNA-containing material in a first dimension of the N dimensions of the N-dimensional grid;
(f) isolate DNA from the pool;
(g) repeat steps (d)-(f) for any second and further dimension of the N-dimensional grid for a different section of the seedling;
(h) amplify the pooled DNA with a set of primers that amplify (part of) the DNA containing the position of the mutation of interest, whereby at least one of the primers contains a pool-specific tag, to obtain reaction products for each of the pools;
(i) pool the reaction products;
(j) determine the nucleotide sequence of the reaction products;
(k) deconvolute the sequences from the pool of step (h) using the pool-specific tags to identify each plant (or seedling) in the grid.
(l) Select the plants (or seedlings) that carry the desired mutation.

The method of the present invention is directed to the introduction and selection of a specific mutation in plants. Preferably the mutation is a stable mutation, i.e. will be inherited indefinitely over generations of conventional crossing. The specific mutation is preferably located in a gene or at least a coding region. Typically the mutation that will be selected is located in the protein-coding region of a gene of interest. Likewise the selected mutation can be located in any other DNA sequence that is not coding for protein but represents any other desirable or undesirable function such as gene regulatory sequences, promoters, enhancers, etc. The gene can be selected from virtually any gene of interest such as a resistance gene or a disease related gene, yield or any developmental, physiological or biochemical function for which a specific gene is known, including its gene regulatory sequences, promoters, enhancers, etc. Preferably, the mutation is located in a genetic region of interest. The selection of the specific mutation can be performed without any prior phenotypic characterization, i.e. without prior analysis whether the introduced mutation leads or does not lead to a change in the phenotype of the plant.

The invention also provides a first step in the analysis of gene function by permitting identification of a mutation in a gene of interest which may not have an ascribed function, but for which at least some nucleotide sequence information is known, i.e., at least enough to provide a unique probe for the gene. The invention thus provides a reverse genetic tool similar to TILLING and KeyPoint that can be applied in any species of plant.

Thus, in the first step, a plurality of mutagenised seeds is provided. Such a plurality can be at least 100 seeds, or at least 1000 seeds or even as large as at least 5000 or 50,000 seeds, depending on the case at hand. The seeds can be from any plant. The seeds can be mutagenised by any known means, but with a preference for chemical means. The plurality of seeds can for instance be made up of batches of seeds, whereby each batch has been mutagenised using the same or different mutagenizing means or that has been subjected to subsequent or parallel mutagenisations. Mutagenizing means in the terms of the present invention are chemical or physical means and are for instance selected form amongst for instance a chemical agent such as ethyl methanesulfonate (EMS), DMS, N-ethyl-N-nitrosourea (ENU), N-methyl-N-nitrosourea (MNU), PRC, methyl methanesulfonate (MMS), chlorambucil, melphalan, sodium azide, ethidium bromide, bromouracil, bromine or nitrous acid, procarbazine hydrochloride, cyclophosphamide, diethyl sulfate, acrylamide monomer, triethylene melamin (TEM), nitrogen mustard, vincristine, dimethylnitrosamine, N-methyl-N'-nitro-Nitrosoguanidine (MNNG), 7,12 dimethylbenz(a)anthracene (DMBA), ethylene oxide, hexamethylphosphoramide (HMPA), bisulfan, diepoxybutane (DEB).

In general, X-rays, gamma rays, neutrons, etc., cause DNA breakage. Cellular repair mechanisms of DNA breaks result in regions of DNA which contain large lesions, including rearrangements and deletions. Although analysis of other types of mutations are preferred according to the invention, analysis of radiation induced mutations, which tend to be larger in that they encompass more bases, are also encompassed by the invention. UV light-induced mutations are largely single nucleotide alterations.

In a preferred embodiment, the mutated organism has been mutagenized such that at least about 1 mutation occurs in every 10,000-1,000 genes. Preferably, the mutagenizing step in comprises inducing a (genetic) mutation into a gene of interest in an organism at an average frequency of $1/500$, preferably $1/100$, more preferably $1/10$ organisms. The mutagenisation procedure can be adapted to achieve these rates, for instance by prolonging the exposure to the mutagenizing means. Preferably, the mutation in any of the above-described methods is a single base pair mutation or a short insertion or deletion mutation, for example, in the range of about 1-10 base pairs The seeds are subsequently grown in an N-dimensional grid. The grid is at least 1D, i.e. N>=1, with N=1 implying analysis of single plants individually The grid can have higher dimensions if desired or considered useful, depending on the case at hand as the more dimensions are seen to carry a specific mutation, the higher the possibility that it is heritable. In practice, there will be a trade off between sequencing costs (higher with larger N because of the increased redundancy required) and confidence levels for heritability. At which N the optimum will be can be determined on a case by case basis, but typically N>=3 is preferred. In a preferred embodiment, N is selected from the group consisting of 3, 4, 5, 6, 7, 8, 9, 10, preferably 3, 4, 5, 6, more preferably 3. From the seeds, seedlings are grown into plants. The seedlings (or parts of the resulting plants) can be sampled for instance by taking leaf or flower punches, but if possible entire true leaves or flowers are preferred. From each plant or seedling, a sample of DNA-containing material is taken from one section of the plant. For each plant or seedling obtained from sowing the mutagenised seeds, the sample is taken from the same section, for instance from the first true leaf or the first flower. For each dimension in the grid, DNA-containing material is sampled. For each dimension, the DNA-containing material is sampled from another section of the plant. Thus, for the second dimension, the material is sampled from, for instance, the second true leaf etc. In one embodiment of the invention, each of the sections of the plant is independently selected from the flowers, leaves, branches, stem or other parts of the plant located above ground and combinations thereof. In one embodiment of the invention the section is a leaf, preferably a true leaf. In one embodiment of the invention, the section for the first dimension of the grid is the first true leaf, for the second dimension is the second true leaf, for the third dimension is the third true leaf.

The DNA-containing material is pooled, whereby each section is pooled in one dimension of the pool. Thus, for a 3-dimensional grid, the DNA-containing material from the first section of the plants is pooled in the first dimension of the pool, the DNA-containing material from the second section of the plants is pooled in the second dimension of the pool etc. subsequently the DNA is isolated from the pool, using any conventional method and means for the isolation of DNA.

The pooled DNA can now be amplified using conventional means for the amplification of DNA, such as PCR, but other technologies may suffice as well. In the case of PCR amplification, the pooled DNA is amplified with a set of primers that amplify (or span) (part of) the DNA containing the region or gene of interest. Preferably at least one of the primers contains a tag, preferably a nucleotide tag that identifies the pool. In this way reaction products are obtained for each of the pools, whereby the reaction products can be linked to the pool from which they were amplified using the pool-specific tag. Thus a pool of reaction products is now obtained, all containing DNA-fragments, stemming from different plants and possibly containing a variety of mutations in the region of interest.

The term 'tag' or 'nucleotide tag', verb 'tagging' refers to the addition of a tag to a nucleic acid sample in order to be able to distinguish it from a second or further nucleic acid sample or amplification product. Tagging can e.g. be performed by the addition of a sequence identifier during amplification or by any other means known in the art. Such sequence identifier can e.g. be a unique base sequence of varying but defined length uniquely used for identifying a specific nucleic acid sample. Typical examples thereof are for instance ZIP sequences. Using such tag, the origin of a sample can be determined upon further processing. In case of combining processed products originating from different nucleic acid samples, the different nucleic acid samples can be identified using different tags. Sometimes the tag is also called an identifier sequence. As discussed above, such identifier sequence may be of varying length depending on the amount of nucleic acid samples to be compared. A length of about 4 bases ($4^4$=256 different tag sequences possible) is usually sufficient to distinguish between the origin of a limited number of samples (up to 256), although it is preferred that the tag sequences differ by more than one base between the samples to be distinguished. As needed, the length of the tag sequences can be adjusted accordingly. The tag is located preferably at the 5' end of the primer.

The reaction products can now be pooled if desired and subjected to sequencing. Sequencing can be performed using any known method for sequencing in the art. In view of the large numbers of sequences that have to be sequenced it is preferred that high throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helios, Solexa, US Genomics, etcetera, which are herein incorporated by reference. The 454 technology described currently allows sequencing of up to 100 million bases in a single run and is 100 times faster and cheaper than competing technology. This will increase with increasing read length per reaction and/or increasing numbers of parallel reactions. The sequencing technology roughly consists of 5 steps: 1) fragmentation of DNA and ligation of specific adaptor to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiterPlate®; and 5) simultaneous sequencing in a plurality of wells by generation of a pyrophosphate light signal.

After sequencing, the sequences of the fragments that are directly obtained from the sequencing step may be trimmed, preferably in silico, to remove any bead annealing sequence, sequencing primer, or adaptor related sequence information. By doing this in silico, the information provided by the tag may be preserved in a separate database field so as to later on connect the discovered heritable mutation (gene) to the address in the DNA pools.

Typically, the alignment or clustering is performed on sequence data that have been trimmed for any added adaptors/primer and/or identifier sequences i.e. using only the sequence data from the fragments that originate from the nucleic acid sample.

Methods of alignment of sequences for comparison purposes are well known in the art. Various programs and alignment algorithms are described in: Smith and Waterman (1981) Adv. Appl. Math. 2:482; Needleman and Wunsch (1970) J. Mol. Biol. 48:443; Pearson and Lipman (1988) Proc. Natl. Acad. Sci. USA 85:2444; Higgins and Sharp (1988) Gene 73:237-244; Higgins and Sharp (1989) CABIOS 5:151-153; Corpet et al. (1988) Nucl. Acids Res. 16:10881-90; Huang et al. (1992) Computer Appl. in the Biosci. 8:155-65; and Pearson et al. (1994) Meth. Mol. Biol. 24:307-31, which are herein incorporated by reference. Altschul et al. (1994) Nature Genet. 6:119-29 (herein incorporated by reference) present a detailed consideration of sequence alignment methods and homology calculations.

The NCBI Basic Local Alignment Search Tool (BLAST) (Altschul et al., 1990) is available from several sources, including the National Center for Biological Information (NCBI, Bethesda, Md.) and on the Internet, for use in connection with the sequence analysis programs blastp, blastn, blastx, tblastn and tblastx. It can be accessed at <http://www.ncbi.nlm.nih.gov/BLAST/>. A description of how to determine sequence identity using this program is available at <http://www.ncbi.nlm.nih.gov/BLAST/blast_help.html>.

The database preferably comprises EST sequences, genomic sequences of the species of interest and/or the non-redundant sequence database of GenBank or similar sequence databases.

High throughput sequencing methods can be used as described in Shendure et al. *Science*, Vol 309, Issue 5741, 1728-1732. Examples thereof are microelectrophoretic sequencing, Hybridization sequencing/sequencing by hybridization (SBH), cyclic-array sequencing on amplified molecules, cyclic-array sequencing on single molecules, non-cyclical, single-molecule, real-time methods, such as, polymerase sequencing, exonuclease sequencing, nanopore sequencing.

For an optimal result, it is of interest that the fragments or the amplified products are sequenced with sufficient redundancy. Redundancy is what enables making the distinction between sequencing errors and genuine genome sequences. In certain embodiments, the redundancy of the sequencing is preferable at least 4, more preferably at least 5, but, redundancies of more than 6, preferably more than 8 or even more than 10 are considered advantageous, although not essential for the inventive concept.

In a subsequent step after sequencing, each seedling in the grid is identified by the deconvolution of the sequences of step (h) by using the pool specific tags. For each seedling or plant is determined whether the combination of the same mutation and the pool-associated tag can be retrieved commensurate with the number of dimensions of the grid. In other words, if the grid contains three dimensions, and the same mutation is retrieved three times together with three tags that identify a pool address that is linked to a particular seedling or plant, the induced mutation has likely been introduced in a manner that is considered for further processing. See also the schematic representation of the method in FIG. 1. These selected seedlings or plants may be grown and the inheritance of the mutation can be confirmed in a following generation. The seedling or plant may also be grown and used in breeding. The selected seedling or plant can now be analysed for the presence or absence of a phenotype of interest, in other words, the selected mutations can be assessed whether it is capable of providing a different phenotype or that the mutation is indifferent to the phenotype studied. Part of the original population of the mutagenised seeds that do not carry a mutation in the region of interest that is heritably present, i.e. is retrieved in every section of the plant that is analysed, can be discarded.

DESCRIPTION OF THE FIGURES

FIG. 1 Schematic representation of the method of sampling and distribution over the grid FIG. 2 chimaerism patterns in mutants for AN1 and RT. Circles correspond to flower corollas. Black indicates mutant tissue, white indicates wild type tissue. Each vertical stack of circles denotes an inflorescence, with the bottom circle being the first flower formed and the top circle the 5th flower. Partially black circles depict chimaeric flowers, with the actual pigmentation pattern as observed in the greenhouse.

FIG. 3 positions of EMS-induced point mutations as detected by Sanger sequencing of individual F1-mutant plants for the gene RT. Mutations are indicated in red, with the canonical WT nucleotide in turquoise.

FIG. 4 Fragment of the RT gene, used for high throughput mutation analysis. Arrows denote the primers used for amplification of this fragment from pools of genomic DNA (see also table 1). Nucleotides marked black are positions of mutations in phenotypically selected EMS mutants m2 and m17, with the base change indicated in brackets.

FIG. 5 Results of high throughput sequence analysis of pooled plants in a three-coordinate grid. The X-axis denotes the coordinate axes (X, Y, Z, respectively in black, grey and striped). The Y-axis denotes the number of times a specific point-mutation of the RT fragment occurred in the sequence reads derived from each coordinate. It can be seen that for the two mutants m2 and m17, a unique combination of three (X,Y,Z) coordinates stands out from background. These combinations correspond to single plants, and match the predetermined positions of these mutants in the grid.

EXAMPLES

Mutagenesis and Analysis of Chimaerism

Figure 2:
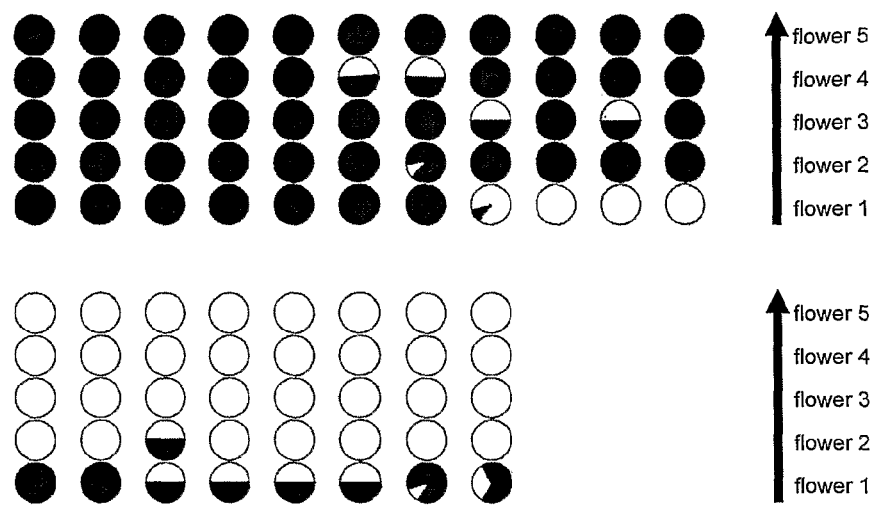

To demonstrate the described method and to estimate the tissue sampling parameters that contribute to its success, we used a genetic scheme in *Petunia hybrida*, as depicted in FIG. 2. A magenta flowering F1 hybrid *Petunia* was produced from a cross between the inbred lines W5 (act1, AN1::dTph1, rt::dTph3) and M1 (act1, AN1, RT), resulting in a doubly heterozygous genotype carrying a recessive allele at two flower color genes (AN1, rt). One of these two genes (AN1) is a transcription factor required for the production of anthocyanin pigments in the corolla (Spelt et al. 2000). Null mutants at AN1 give rise to white flowers. The second gene (RT) is UDP rhamnose: anthocyanin-3-glucoside rhamnosyl transferase. In the genetic background used here, null mutants of RT produce red flowers, as a consequence of the accumulation of cyanidin-3-glucoside (Kroon et al. 1994, Brugliera et al. 1994). Note that both recessive color markers are transposon insertion alleles carrying dTph1 and dTph3 insertions respectively (Spelt et al. 2000, Kroon et al. 1994). Transposition of these elements does not occur because both parental lines and F1 hybrid lack the activator of dTph1 (act1, Stuurman and Kuhlemeier 2005 The Plant Journal Volume 41 Issue 6, Pages 945-955) while dTph3 is transposition deficient (Kroon et al. 1994). Upon mutagenic treatment of F1 hybrid seeds with ethylmethanesulfonate (EMS), some of the resulting plants will carry novel mutations in the wild type alleles of AN1 or RT. Such plants will be chimaeras, and can be visually identified by a proportion of white or red corollas or corolla parts on a magenta background.

A population of 3600 F1 plants was grown from EMS treated seed, and the sectoring patterns for flower color were recorded visually on the primary inflorescence only. The primary inflorescence is defined as clonally derived from the embryonic shoot apical meristem, as opposed to secondary inflorescences which grow from axillary meristems and are clonally derived from their subtending leaf (Furner and Pumfrey 1992). The results are schematically given in FIG. 2. A total of 19 mutants were observed for AN1 and RT together. As can be seen, chimaerism followed a predictable pattern in that only large sectors occurred (mostly half flowers) and that chimaerism gradually disappeared with the age of the inflorescence. After 5 flowers had been produced, chimaerism was lost and plants had either stably acquired the mutant color or went on as fully wild type. Stable mutants and wild types were approximately equal in number, probably reflecting two unstable initial cells (stem cells) in the embryonic apical meristem It is concluded from these data that a large, seed-mutagenized F1 population of *Petunia* can be treated as non-chimaeric after the 5th flower on the primary inflorescence. Practically, this implies that if mutations are to be sought in specific genes, by any DNA screening method, it would suffice to sample inflorescence tissue from nodes at or after this stage. If these samples show a particular point mutation, the plant will stably carry the mutation in all tissues and branches that develop subsequently. As can be seen from FIG. 2, sampling may also be done earlier, e.g. after the 2nd flower, with a fairly good chance of identifying individuals that will develop as stable mutants Molecular Confirmation of Mutations by Sanger Sequencing To demonstrate that the phenotypic screen for flower color was due to mutations in the genes AN1 or RT, bracts from the 5th inflorescence node of fully mutant F1 individuals were taken for isolation of genomic DNA and analysis of gene sequences. The RT gene does not contain introns, allowing the entire coding sequence of ~1.5 kb to be PCR amplified with a single primer pair. For convenience, only RT was analyzed in detail and results are assumed assumed to apply to AN1 by analogy. Primers for RT were designed in such a way, that only the allele from the M1 parent was amplified and not from the W5 parent. This specificity is based on natural RT sequence polymorphisms between the two parents, for which the designed oligonucleotide primers could discriminate (not shown). This allowed for the sequencing of exclusively EMS-induced alleles from the M1 parent, and not the transposon insertion alleles that were present in line W5.

Conventional Sanger sequencing of the entire RT coding region in all 7 red-flowering F1 mutants was performed on PCR products that were cloned into a bacterial plasmid vector. For each mutant F1 plant, RT products in 20 independent recombinant plasmids were sequenced. This analysis revealed point mutations in all but one F1 plant. The kind and position of these mutations is given in FIG. 3.

However, in all F1 plants, not all of 20 recombinant plasmids showed the mutation, with frequencies ranging from 3 to 6 mutant inserts per plant. This indicates that the sampled tissue was not genotypically homogeneous for the mutant allele. Given that the plants were phenotypically homogeneous, the F1 mutants were thus periclinal chimaeras carrying a mutation in one of the three clonal cell layers L1, L2, L3 that are the histogenic basis of the plant body. The L1 layer constitutes the epidermis of the flower corolla, and it is well known that anthocyanin pigmentation is restricted to the epidermis (refs). Thus, the analyzed RT mutants contained a fully mutant L1 layer, but a wild type L2 and L3 layer.

It is concluded that phenotypic F1 mutant selection identified periclinal chimaeras, and that point mutations were found in the predicted genes. Thus, when genotypic mutation screening is done on all 3600 F1 plants and a particular mutation is found in at least two consecutive floral nodes beyond the 4th node on the primary inflorescence of one individual plant, that plant is a stable periclinal chimaera in (at least) one of the three cell-layers L1, L2 or L3.

High Throughput Sequencing Identifies Mutants Correctly

To further demonstrate that the current invention allows for the F1-selection of mutations in specific genes in a high-throughput mode, sequencing technology of 454 Life Sciences (Margulies et al. 2005) was used to analyze RT amplicon sequences in a large set of individual plants. A subset of 1440 plants, taken from the total of 3600 EMS-mutagenized F1 hybrids, was arranged in a grid in the greenhouse. The grid consisted of three coordinate axes (x, y, z=rows, blocks, columns) with 35 coordinates (x1-x9, y1-y10, z1-z16) totalling 9×10×16=1440 individual plants. Each plant in the grid corresponds to a unique (x,y,z) combination of one coordinate in each of the three axes. In this group of 1440 plants, two periclinal RT mutants (m2 and m17 of FIG. 3) were included and positioned on a unique, known location (m2=X10, Y2, Z8; m17=X1, Y1, Z2). These mutants were selected to contain contain EMS-induced point mutations within a 199 base-pairs segment of the RT gene, which is within the average read length of a GS-FLX Genome Sequencer (Roche, 454 Life Sciences).

Tissue sampling was done from bracts on the 4th, 5th and 6th floral nodes on the inflorescence of all 1440 plants in the grid, with the 4th node representing the blocks, the 5th node the rows, and the 6th node the columns. Care was taken to take equal amounts of tissue for each plant and each sample. Tissue samples were pooled according to their coordinate, resulting in 9+10+16=35 tissue pools. These pooled tissues were homogenized, followed by extraction of genomic DNA. All 1440 plants are thus represented by 35 DNA samples. The level of pooling thus corresponds to 1440/9=160 plants per row, 1440/10=144 plants per block, and 1440/16=90 plants per column.

Of each of these 35 DNA samples, a specific 199 by segment (FIG. 4) of the RT gene was amplified by PCR using RT-specific primers. These primers were extended at their 5' ends by a specific 5-base nucleotide sequence (henceforth termed tag), with each of the 35 coordinates in the grid defined by a different sequence of the tag. Primers were designed so as to amplify only the RT allele derived from the M1 parent, which must carry the EMS-induced point mutations identified by the phenotypic screening. The resulting set of 35 PCR products are mixtures of products from the individual plants that constituted the DNA samples. All 35 PCR products were pooled and sequenced on a GS-FLX Genome Analyzer (Roche) to produce a total of 549646 individual sequence reads. Because individual reads carry a coordinate-specific 5'-tag immediately preceding the sequence of the RT-specific amplification primers, they can be assigned to one of the 35 single coordinates of the grid. If a particular sequence variant (i.e. EMS-induced point mutation) occurs in a unique combination of the three coordinate axes (e.g. x1, y1, z1), this variant can be assigned as a true point mutation to one individual plant. All other mutations, which occur in just one (or rarely in two) coordinate must be sequencing errors, provided that DNA samples are taken from tissue beyond the 4th inflorescence node, in this particular example of Petunia.

For the two RT mutants with known sequence (m1, m2, and m17, FIG. 3) that were included in the grid on predetermined positions, their particular nucleotide mutation was searched for in the dataset of sequences by looking for a perfect match of a 12 base sequence string that included the mutant base. These searches were done for both the forward (5'→3') orientation and the reverse complement (3'→5'). Subsequently, of the sequence reads that contained the mutant base, the 5-base tags were identified and counted. As can be seen from FIG. 5, the positions of these plants could be readily identified by a unique combination of (x,y,z) coordinates, in which the mutation occurred much more frequently than in any other coordinate. These data indicate that the stably mutant plants can be correctly identified from a total of 1440 plants in the absence of any phenotypic selection. This number This number of plants can be increased.

Materials and Methods

EMS Mutagenesis 360 mg dry *petunia* seed (approximately 5000 seeds) of the (W5×M1) F1 hybrid was submerged in 5 ml 0.5% (v/v) ethylmethanesulfonate (EMS, Sigma-Aldrich) in a 10 ml tube, and mixed thoroughly. Seeds were left in EMS solution for 14 hours at room temperature. Seeds were then washed thoroughly with 10 times 10 ml of water, and sown on soil. After seedlings had produced the first two true leaves they were transplanted into 40 pot (8×5) trays and arranged in a three dimensional grid in a greenhouse in January 2008. They were grown at 16 hrs light at 24° C.

Sanger Sequencing of Chimaeric RT Mutant Plants

Bract tissue subtending the 5th flower was harvested of an individual plant. Total genomic DNA was isolated using a Qiagen DNeasy Plant Mini Kit. The complete RT coding sequence was PCR amplified using primers 08A281 and 08A282 (see table 1) which are located in the 5' and 3' non-coding leader and trailer of the RT gene respectively. Reactions consisted of 25 pmol of each primer, 0.2 mM dNTP, 1× PCR buffer, 50 ng genomic DNA, 1 unit AmpliTaq Gold DNA polymerase (Applied Biosystems) in a total volume of 50 microliter. Thermal cycling was done after an initial 10 minutes at 95° C. for 35 cycles of 30 sec 95° C., 60 sec 55° C., 60 sec 72° C., followed by a final extension of 6 min. 72° C. Products were checked for being a single band on agarose gel electrophoresis, and cloned in a bacterial plasmid vector. Recombinant plasmids from twenty randomly picked colonies were sequenced using an automated capillary sequencer using standard Sanger chain terminator methodology. An EMS-induced mutation (SNP) was declared if the same base change occurred more than twice in the set of 20 sequences.

High Throughput Mutation Detection by GS FLX Sequencing Technology

Plants were kept in a strictly maintained position in the greenhouse. Bracts subtending the 4th, 5th or 6th flower were harvested for each individual plant and pooled according to the 35 coordinates in the system. All 35 pools of bract tissue were homogenized in liquid nitrogen and stored at −80° C. Samples of tissue powder were taken for isolation of total genomic DNA using a Qiagen DNeasy Plant Mini Kit. PCR amplification of a single segment of the RT gene was done using the primers listed in table 1. For each of the 35 coordinates, a pair of forward and reverse primers was used that carried the same 5-base tag, such that each coordinate is specified by a single tag on both ends of the PCR product. Reactions were carried out with 30 ng genomic DNA, 0.5 mM dNTPs, 25 pmol of each primer, 1 unit AmpliTaq DNA polymerase (Applied Biosystems) in a total volume of 25 microliter. Cycling was done with an initial 5 min. 95° C., followed by 35 cycles of 30 sec 94° C., 30 sec 65° C. and 30 sec 72° C. PCR products were purified using the QIAquick PCR purification kit (Qiagen), and checked for being a single band after agarose gel electrophoresis.

All 35 PCR products were made blunt by incubation with 0.5 unit Klenow enzyme in the presence of 1 mM dNTPs in a total volume of 40 microliter for 15 minutes at 25° C. Reactions were stopped by adding EDTA to a final concentration of 10 mM, followed by heating at 72° C. for 20 minutes. Samples were then purified using the QIAquick PCR purification kit (Qiagen) and eluted in 10 mM Tris pH=8.5. All 35 blunt-ended products were subsequently 5'-phosphorylated by incubation with 20 units T4 polynucleotide kinase in the presence of 0.25 mM ATP in total volume of 40 microliter for 30 minutes at 37° C., followed by purification using the QIAquick PCR purification kit (Qiagen) and eluted in 10 mM Tris pH=8.5.

Blunt-ended, phosphorylated amplification products from the 3D pools were subjected to high throughput sequencing on a GS-FLX sequencer (Roche) using 454 Life Sciences technology as described by Margulies et al. (2005). All 35 PCR products were separately ligated to 454 adaptor sequences, by incubating 50 ng PCR product in 1× ligase buffer (Roche Life Sciences, GS DNA library preparation kit), 0.1 microliters of adapter (Roche Life Sciences, GS DNA library preparation kit) and 1 Weiss unit T4 DNA ligase, in a total volume of 12 microliters for 4 hours at 25° C. Subsequently, ligated products were subjected to PCR amplification using standard PCR amplification primers (Roche Life Sciences GS, DNA library preparation kit). Cycling was done with 4 microliter of ligation mix, 0.5 mM dNTPs, 25 pmol of each primer, 1 unit AmpliTaq DNA polymerase (Applied Biosystems) in a total volume of 25 microliter. Cycling was done with an initial 60 sec. 72° C., 5 min. 95° C., followed by 25 cycles of 30 sec 94° C., 30 sec 55° C. and 30 sec 72° C. Amplification products were analyzed by agarose gel electrophoresis, and pooled into one final sample. This sample was then processed and sequenced using GS-FLX equipment (Roche Life Sciences) according to the instructions of the manufacturer.

To detect mutations among the sequence output, raw sequences (549646 reads) were searched for the presence of the SNP mutation present in mutants m2 and m17. Searches were performed by identifying a 100% match to the strings "m2 forward": GGTTTAGTTCAG [SEQ ID 1] and "m2 reverse": CTGAACTAAACC [SEQ ID 2] and "m17 forward": GGTGACCAGATT [SEQ ID 3] and "m17 reverse": AATCTGGTCACC[SEQ ID 4]. Reads that matched these strings were grouped according the sequence of their 5' tag for coordinate identification, and counted. Counts were then displayed as in FIG. 5.

REFERENCES

Spelt C, Quattrocchio F, Mol J N, Koes R. (2000) Anthocyanin1 of *petunia* encodes a basic helix-loop-helix protein that directly activates transcription of structural anthocyanin genes. Plant Cell 12(9):1619-32.

Brugliera F, Holton T A, Stevenson T W, Farcy E, Lu C Y, Cornish E C. (1994) Isolation and characterization of a cDNA clone corresponding to the Rt locus of *Petunia hybrida*. Plant J. 5(1):81-92.

Kroon J, Souer E, de Graaff A, Xue Y, Mol J, Koes R. (1994) Cloning and structural analysis of the anthocyanin pigmentation locus Rt of *Petunia hybrida*: characterization of insertion sequences in two mutant alleles. Plant J. 5(1):69-80.

Furner I. J., Pumfrey J. E. (1992) Cell fate in the shoot apical meristem of *Arabidopsis thaliana*. Development 115, 755-764

Margulies M, Egholm M, Altman W E, Attiya S, Bader J S, et al. (2005) Genome sequencing in microfabricated high-density picoliter reactors. Nature 437:376-80

TABLE 1

DNA oligonucleotides used for Sanger-based re-sequencing of RT mutant alleles, and for high throughput mutation screening by KeyPoints. In the latter, the first 5 bases at the 5' end (in bold) are unique for a single coordinate in the 3D matrix pooling system. Tags are linked to these coordinates as indicated in the last column, in which (1-16), (A-J) and (I-X) denote coordinates in each of the 3 axes of the matrix.

| primer list Sanger sequencing | | |
|---|---|---|
| 08A281 | CCAATAATGAACGCTTGCTCGCAG | [SEQ ID 5] |
| 08A282 | GCATCAGAATGCTGGGAACATCG | [SEQ ID 6] |

TABLE 1-continued

DNA oligonucleotides used for Sanger-based re-sequencing of RT mutant alleles, and for high throughput mutation screening by KeyPoints. In the latter, the first 5 bases at the 5' end (in bold) are unique for a single coordinate in the 3D matrix pooling system. Tags are linked to these coordinates as indicated in the last column, in which (1-16), (A-J) and (I-X) denote coordinates in each of the 3 axes of the matrix.

primer list KeyPoints

| FORWARD | | | REVERSE | | |
|---|---|---|---|---|---|
| 08Z848 | ACACGTCCACCCCAGCTTCCATATCACC | [SEQ ID 7] | 08Z888 | ACACGTCATTCAGGTTGGGTGCAACAGC | [SEQ ID 47] | 1 |
| 08Z849 | ACATCTCCACCCCAGCTTCCATATCACC | [SEQ ID 8] | 08Z889 | ACATCTCATTCAGGTTGGGTGCAACAGC | [SEQ ID 48] | 2 |
| 08Z850 | ACGACTCCACCCCAGCTTCCATATCACC | [SEQ ID 9] | 08Z890 | ACGACTCATTCAGGTTGGGTGCAACAGC | [SEQ ID 49] | 3 |
| 08Z851 | ACGCTTCCACCCCAGCTTCCATATCACC | [SEQ ID 10] | 08Z891 | ACGCTTCATTCAGGTTGGGTGCAACAGC | [SEQ ID 50] | 4 |
| 08Z852 | ACTGCTCCACCCCAGCTTCCATATCACC | [SEQ ID 11] | 08Z892 | ACTGCTCATTCAGGTTGGGTGCAACAGC | [SEQ ID 51] | 5 |
| 08Z853 | AGAGCTCCACCCCAGCTTCCATATCACC | [SEQ ID 12] | 08Z893 | AGAGCTCATTCAGGTTGGGTGCAACAGC | [SEQ ID 52] | 6 |
| 08Z854 | AGATGTCCACCCCAGCTTCCATATCACC | [SEQ ID 13] | 08Z894 | AGATGTCATTCAGGTTGGGTGCAACAGC | [SEQ ID 53] | 7 |
| 08Z855 | AGCATTCCACCCCAGCTTCCATATCACC | [SEQ ID 14] | 08Z895 | AGCATTCATTCAGGTTGGGTGCAACAGC | [SEQ ID 54] | 8 |
| 08Z856 | AGCTCTCCACCCCAGCTTCCATATCACC | [SEQ ID 15] | 08Z896 | AGCTCTCATTCAGGTTGGGTGCAACAGC | [SEQ ID 55] | 9 |
| 08Z857 | AGTAGTCCACCCCAGCTTCCATATCACC | [SEQ ID 16] | 08Z897 | AGTAGTCATTCAGGTTGGGTGCAACAGC | [SEQ ID 56] | 10 |
| 08Z858 | AGTCTTCCACCCCAGCTTCCATATCACC | [SEQ ID 17] | 08Z898 | AGTCTTCATTCAGGTTGGGTGCAACAGC | [SEQ ID 57] | 11 |
| 08Z859 | ATACTTCCACCCCAGCTTCCATATCACC | [SEQ ID 18] | 08Z899 | ATACTTCATTCAGGTTGGGTGCAACAGC | [SEQ ID 58] | 12 |
| 08Z860 | ATCAGTCCACCCCAGCTTCCATATCACC | [SEQ ID 19] | 08Z900 | ATCAGTCATTCAGGTTGGGTGCAACAGC | [SEQ ID 59] | 13 |
| 08Z861 | ATCGTTCCACCCCAGCTTCCATATCACC | [SEQ ID 20] | 08Z901 | ATCGTTCATTCAGGTTGGGTGCAACAGC | [SEQ ID 60] | 14 |
| 08Z862 | ATGATTCCACCCCAGCTTCCATATCACC | [SEQ ID 21] | 08Z902 | ATGATTCATTCAGGTTGGGTGCAACAGC | [SEQ ID 61] | 15 |
| 08Z863 | ATGTGTCCACCCCAGCTTCCATATCACC | [SEQ ID 22] | 08Z903 | ATGTGTCATTCAGGTTGGGTGCAACAGC | [SEQ ID 62] | 16 |
| 08Z864 | CACGTTCCACCCCAGCTTCCATATCACC | [SEQ ID 23] | 08Z904 | CACGTTCATTCAGGTTGGGTGCAACAGC | [SEQ ID 63] | A |
| 08Z865 | CACTGTCCACCCCAGCTTCCATATCACC | [SEQ ID 24] | 08Z905 | CACTGTCATTCAGGTTGGGTGCAACAGC | [SEQ ID 64] | B |
| 08Z866 | CAGATTCCACCCCAGCTTCCATATCACC | [SEQ ID 25] | 08Z906 | CAGATTCATTCAGGTTGGGTGCAACAGC | [SEQ ID 65] | C |
| 08Z867 | CAGCGTCCACCCCAGCTTCCATATCACC | [SEQ ID 26] | 08Z907 | CAGCGTCATTCAGGTTGGGTGCAACAGC | [SEQ ID 66] | D |
| 08Z868 | CATAGTCCACCCCAGCTTCCATATCACC | [SEQ ID 27] | 08Z908 | CATAGTCATTCAGGTTGGGTGCAACAGC | [SEQ ID 67] | E |
| 08Z869 | CATGCTCCACCCCAGCTTCCATATCACC | [SEQ ID 28] | 08Z909 | CATGCTCATTCAGGTTGGGTGCAACAGC | [SEQ ID 68] | F |
| 08Z870 | CGACTTCCACCCCAGCTTCCATATCACC | [SEQ ID 29] | 08Z910 | CGACTTCATTCAGGTTGGGTGCAACAGC | [SEQ ID 69] | G |
| 08Z871 | CGATCTCCACCCCAGCTTCCATATCACC | [SEQ ID 30] | 08Z911 | CGATCTCATTCAGGTTGGGTGCAACAGC | [SEQ ID 70] | H |
| 08Z872 | CGCAGTCCACCCCAGCTTCCATATCACC | [SEQ ID 31] | 08Z912 | CGCAGTCATTCAGGTTGGGTGCAACAGC | [SEQ ID 71] | J |
| 08Z873 | CGCGCTCCACCCCAGCTTCCATATCACC | [SEQ ID 32] | 08Z913 | CGCGCTCATTCAGGTTGGGTGCAACAGC | [SEQ ID 72] | I |
| 08Z874 | CGTATTCCACCCCAGCTTCCATATCACC | [SEQ ID 33] | 08Z914 | CGTATTCATTCAGGTTGGGTGCAACAGC | [SEQ ID 73] | II |
| 08Z875 | CGTCGTCCACCCCAGCTTCCATATCACC | [SEQ ID 34] | 08Z915 | CGTCGTCATTCAGGTTGGGTGCAACAGC | [SEQ ID 74] | III |
| 08Z876 | CTAGTTCCACCCCAGCTTCCATATCACC | [SEQ ID 35] | 08Z916 | CTAGTTCATTCAGGTTGGGTGCAACAGC | [SEQ ID 75] | IV |
| 08Z877 | CTATGTCCACCCCAGCTTCCATATCACC | [SEQ ID 36] | 08Z917 | CTATGTCATTCAGGTTGGGTGCAACAGC | [SEQ ID 76] | V |
| 08Z878 | CTCATTCCACCCCAGCTTCCATATCACC | [SEQ ID 37] | 08Z918 | CTCATTCATTCAGGTTGGGTGCAACAGC | [SEQ ID 77] | VI |
| 08Z879 | CTGAGTCCACCCCAGCTTCCATATCACC | [SEQ ID 38] | 08Z919 | CTGAGTCATTCAGGTTGGGTGCAACAGC | [SEQ ID 78] | VII |
| 08Z880 | CTGCTTCCACCCCAGCTTCCATATCACC | [SEQ ID 39] | 08Z920 | CTGCTTCATTCAGGTTGGGTGCAACAGC | [SEQ ID 79] | VIII |
| 08Z887 | TATCGTCCACCCCAGCTTCCATATCACC | [SEQ ID 40] | 08Z927 | TATCGTCATTCAGGTTGGGTGCAACAGC | [SEQ ID 80] | IX |
| 08Z885 | TAGTCTCCACCCCAGCTTCCATATCACC | [SEQ ID 41] | 08Z925 | TAGTCTCATTCAGGTTGGGTGCAACAGC | [SEQ ID 81] | X |

TABLE 1-continued

DNA oligonucleotides used for Sanger-based re-sequencing of RT mutant alleles, and for high throughput mutation screening by KeyPoints. In the latter, the first 5 bases at the 5' end (in bold) are unique for a single coordinate in the 3D matrix pooling system. Tags are linked to these coordinates as indicated in the last column, in which (1-16), (A-J) and (I-X) denote coordinates in each of the 3 axes of the matrix.

| | | | | |
|---|---|---|---|---|
| 08Z886 | TATACTCCACCCCAGCTTCCATATCACC[SEQ ID 42] | 08Z926 | TATACTCATTCAGGTTGGGTGCAACAGC [SEQ ID 82] | |
| 08Z881 | TACATTCCACCCCAGCTTCCATATCACC[SEQ ID 43] | 08Z921 | TACATTCATTCAGGTTGGGTGCAACAGC [SEQ ID 83] | IX |
| 08Z882 | TACGCTCCACCCCAGCTTCCATATCACC[SEQ ID 44] | 08Z922 | TACGCTCATTCAGGTTGGGTGCAACAGC [SEQ ID 84] | |
| 08Z883 | TAGAGTCCACCCCAGCTTCCATATCACC[SEQ ID 45] | 08Z923 | TAGAGTCATTCAGGTTGGGTGCAACAGC [SEQ ID 85] | |
| 08Z884 | TAGCTTCCACCCCAGCTTCCATATCACC[SEQ ID 46] | 08Z924 | TAGCTTCATTCAGGTTGGGTGCAACAGC [SEQ ID 86] | |

The invention claimed is:

1. Method for the introduction and selection of a specific heritable mutation in M1 plants, comprising:
  (a) providing a plurality of mutagenized seeds;
  (b) sowing the mutagenized seeds;
  (c) growing plants from the seeds;
  (d) sampling DNA-containing material from a first section of the plant;
  (e) pooling the DNA-containing material from each first section, wherein said pooled DNA from the combined pools of the first section comprises the first dimension of a N-dimensional grid;
  (f) isolating DNA from the pool;
  (g) repeating steps (d)-(f) for a second and any further dimension of the N-dimensional grid for a different section of the plant, wherein each section comprises a different growth and/or developmental stage of the plant and each section is pooled into a plurality of pools and the combination of pools for each section comprises its own dimension in the N-dimensional grid; wherein the combination of pools for the $N^{th}$ section constitutes the $N^{th}$ dimension in the N-dimensional grid;
  (h) amplifying each pooled DNA with a set of primers that amplify region of the DNA containing the position of the mutation of interest, whereby at least one of the primers contains a pool-specific tag, to obtain reaction products for each of the pools;
  (i) pooling the reaction products;
  (j) determining the nucleotide sequence of the reaction products;
  (k) deconvoluting the sequences from each pool of step (h) using the pool-specific tags to identify each plant in the grid; and
  (l) selecting an M1 plant having the desired mutation in at least N−1 of the N sampled sections.

2. Method according to claim 1, wherein the selected plants are grown and the inheritance of the mutation is confirmed in a following generation.

3. Method according to claim 1, wherein samples are obtained from at least two sections and N is at least 2.

4. Method according to claim 1, wherein the section of the plant is selected from the flowers, leaves, branches, stem, pollen or other parts of the plant located above ground and combinations thereof.

5. Method according to claim 4, wherein the section is a leaf or a flower.

6. Method according to claim 1, wherein the section for the first dimension of the grid is the first flower or true leaf, the section for the second dimension is the second true leaf, and the section for the third dimension is the third true leaf.

7. Method according to claim 1, wherein the plurality of seeds is at least 100 seeds.

8. Method according to claim 1, wherein the mutagenising agent is a chemical or physical mutagenising agent.

9. Method according to claim 1, wherein the chemical agent is selected from the group consisting of EMS, DMS, ENU, MNU, PRC, DEB, MMS, chlorambucil, melphalan, sodium azide, ethidium bromide, bromouracil, bromine or nitrous acid.

10. Method according to claim 1, wherein the physical mutagenising agent is ionizing radiation.

11. Method according to claim 1, wherein the tag is a nucleotide tag, containing at least 4 nucleotides.

12. Method according to claim 1, wherein the sequencing is based on high-throughput sequencing.

13. Method according to claim 1, wherein the selected plant is correlated to the presence or absence of a desired phenotype.

14. A method for plant breeding, comprising selecting a plant produced by the method of claim 1 and either selfing said plant or crossing said plant with another plant, thereby generating a progeny plant carrying a desired mutation.

15. Method according to claim 1, wherein N is selected from the group consisting of 2, 3, 4, 5, and 6.

16. Method according to claim 1, wherein N is 3.

17. Method according to claim 4, wherein the section is a true leaf.

18. Method according to claim 1, wherein the plurality of seeds is at least 1000 seeds.

19. Method according to claim 1, wherein the plurality of seeds is at least 5000 seeds.

20. Method according to claim 10, wherein the physical mutagenising agent is UV radiation, radioactive alpha or gamma radiation.

21. Method according to claim 11, wherein the nucleotide tag is located at the 5' end of the primer.

* * * * *

UNITED STATES PATENT AND TRADEMARK OFFICE
CERTIFICATE OF CORRECTION

PATENT NO. : 8,716,550 B2  Page 1 of 1
APPLICATION NO. : 12/679565
DATED : May 6, 2014
INVENTOR(S) : Jeroen Stuurman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 744 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 86

<210> SEQ ID NO 1
<211> LENGTH: 12
<212> TYPE: DNA
<213> ORGANISM: Artificial
<220> FEATURE:
<223> OTHER INFORMATION: Primer

<400> SEQUENCE: 1
ggtttagttc ag                                                                12

<210> SEQ ID NO 2
<211> LENGTH: 12
<212> TYPE: DNA
<213> ORGANISM: Artificial
<220> FEATURE:
<223> OTHER INFORMATION: Primer

<400> SEQUENCE: 2
ctgaactaaa cc                                                                12

<210> SEQ ID NO 3
<211> LENGTH: 12
<212> TYPE: DNA
<213> ORGANISM: Artificial
<220> FEATURE:
<223> OTHER INFORMATION: Primer

<400> SEQUENCE: 3
ggtgaccaga tt                                                                12

<210> SEQ ID NO 4
<211> LENGTH: 12
<212> TYPE: DNA
<213> ORGANISM: Artificial
<220> FEATURE:
<223> OTHER INFORMATION: Primer

<400> SEQUENCE: 4
aatctggtca cc                                                                12

<210> SEQ ID NO 5
<211> LENGTH: 24
<212> TYPE: DNA
<213> ORGANISM: Artificial
<220> FEATURE:
<223> OTHER INFORMATION: Primer

```
<400> SEQUENCE: 5
ccaataatga acgcttgctc gcag                                          24

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
gcatcagaat gctgggaaca tcg                                           23

<210> SEQ ID NO 7
<211> LENGTH: 28
<212> TYPE: DNA
<213> ORGANISM: Artificial
<220> FEATURE:
<223> OTHER INFORMATION: Primer

<400> SEQUENCE: 7
acacgtccac cccagcttcc atatcacc                                      28

<210> SEQ ID NO 8
<211> LENGTH: 28
<212> TYPE: DNA
<213> ORGANISM: Artificial
<220> FEATURE:
<223> OTHER INFORMATION: Primer

<400> SEQUENCE: 8
acatctccac cccagcttcc atatcacc                                      28

<210> SEQ ID NO 9
<211> LENGTH: 28
<212> TYPE: DNA
<213> ORGANISM: Artificial
<220> FEATURE:
<223> OTHER INFORMATION: Primer

<400> SEQUENCE: 9
acgactccac cccagcttcc atatcacc                                      28

<210> SEQ ID NO 10
<211> LENGTH: 28
<212> TYPE: DNA
<213> ORGANISM: Artificial
<220> FEATURE:
<223> OTHER INFORMATION: Primer

<400> SEQUENCE: 10
acgcttccac cccagcttcc atatcacc                                      28

<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11
actgctccac cccagcttcc atatcacc                                      28

<210> SEQ ID NO 12
<211> LENGTH: 28
```

```
<212> TYPE: DNA
<213> ORGANISM: Artificial
<220> FEATURE:
<223> OTHER INFORMATION: Primer

<400> SEQUENCE: 12
agagctccac cccagcttcc atatcacc                                         28

<210> SEQ ID NO 13
<211> LENGTH: 28
<212> TYPE: DNA
<213> ORGANISM: Artificial
<220> FEATURE:
<223> OTHER INFORMATION: Primer

<400> SEQUENCE: 13
agatgtccac cccagcttcc atatcacc                                         28

<210> SEQ ID NO 14
<211> LENGTH: 28
<212> TYPE: DNA
<213> ORGANISM: Artificial
<220> FEATURE:
<223> OTHER INFORMATION: Primer

<400> SEQUENCE: 14
agcattccac cccagcttcc atatcacc                                         28

<210> SEQ ID NO 15
<211> LENGTH: 28
<212> TYPE: DNA
<213> ORGANISM: Artificial
<220> FEATURE:
<223> OTHER INFORMATION: Primer

<400> SEQUENCE: 15
agctctccac cccagcttcc atatcacc                                         28

<210> SEQ ID NO 16
<211> LENGTH: 28
<212> TYPE: DNA
<213> ORGANISM: Artificial
<220> FEATURE:
<223> OTHER INFORMATION: Primer

<400> SEQUENCE: 16
agtagtccac cccagcttcc atatcacc                                         28

<210> SEQ ID NO 17
<211> LENGTH: 28
<212> TYPE: DNA
<213> ORGANISM: Artificial
<220> FEATURE:
<223> OTHER INFORMATION: Primer

<400> SEQUENCE: 17
agtcttccac cccagcttcc atatcacc                                         28

<210> SEQ ID NO 18
<211> LENGTH: 28
<212> TYPE: DNA
<213> ORGANISM: Artificial
<220> FEATURE:
<223> OTHER INFORMATION: Primer

<400> SEQUENCE: 18
atacttccac cccagcttcc atatcacc                                         28
```

```
<210> SEQ ID NO 19
<211> LENGTH: 28
<212> TYPE: DNA
<213> ORGANISM: Artificial
<220> FEATURE:
<223> OTHER INFORMATION: Primer

<400> SEQUENCE: 19
atcagtccac cccagcttcc atatcacc                                      28

<210> SEQ ID NO 20
<211> LENGTH: 28
<212> TYPE: DNA
<213> ORGANISM: Artificial
<220> FEATURE:
<223> OTHER INFORMATION: Primer

<400> SEQUENCE: 20
atcgttccac cccagcttcc atatcacc                                      28

<210> SEQ ID NO 21
<211> LENGTH: 28
<212> TYPE: DNA
<213> ORGANISM: Artificial
<220> FEATURE:
<223> OTHER INFORMATION: Primer

<400> SEQUENCE: 21
atgattccac cccagcttcc atatcacc                                      28

<210> SEQ ID NO 22
<211> LENGTH: 28
<212> TYPE: DNA
<213> ORGANISM: Artificial
<220> FEATURE:
<223> OTHER INFORMATION: Primer

<400> SEQUENCE: 22
atgtgtccac cccagcttcc atatcacc                                      28

<210> SEQ ID NO 23
<211> LENGTH: 28
<212> TYPE: DNA
<213> ORGANISM: Artificial
<220> FEATURE:
<223> OTHER INFORMATION: Primer

<400> SEQUENCE: 23
cacgttccac cccagcttcc atatcacc                                      28

<210> SEQ ID NO 24
<211> LENGTH: 28
<212> TYPE: DNA
<213> ORGANISM: Artificial
<220> FEATURE:
<223> OTHER INFORMATION: Primer

<400> SEQUENCE: 24
cactgtccac cccagcttcc atatcacc                                      28

<210> SEQ ID NO 25
<211> LENGTH: 28
<212> TYPE: DNA
<213> ORGANISM: Artificial
<220> FEATURE:
<223> OTHER INFORMATION: Primer
```

```
<400> SEQUENCE: 25
cagattccac cccagcttcc atatcacc                                          28

<210> SEQ ID NO 26
<211> LENGTH: 28
<212> TYPE: DNA
<213> ORGANISM: Artificial
<220> FEATURE:
<223> OTHER INFORMATION: Primer

<400> SEQUENCE: 26
cagcgtccac cccagcttcc atatcacc                                          28

<210> SEQ ID NO 27
<211> LENGTH: 28
<212> TYPE: DNA
<213> ORGANISM: Artificial
<220> FEATURE:
<223> OTHER INFORMATION: Primer

<400> SEQUENCE: 27
catagtccac cccagcttcc atatcacc                                          28

<210> SEQ ID NO 28
<211> LENGTH: 28
<212> TYPE: DNA
<213> ORGANISM: Artificial
<220> FEATURE:
<223> OTHER INFORMATION: Primer

<400> SEQUENCE: 28
catgctccac cccagcttcc atatcacc                                          28

<210> SEQ ID NO 29
<211> LENGTH: 28
<212> TYPE: DNA
<213> ORGANISM: Artificial
<220> FEATURE:
<223> OTHER INFORMATION: Primer

<400> SEQUENCE: 29
cgacttccac cccagcttcc atatcacc                                          28

<210> SEQ ID NO 30
<211> LENGTH: 28
<212> TYPE: DNA
<213> ORGANISM: Artificial
<220> FEATURE:
<223> OTHER INFORMATION: Primer

<400> SEQUENCE: 30
cgatctccac cccagcttcc atatcacc                                          28

<210> SEQ ID NO 31
<211> LENGTH: 28
<212> TYPE: DNA
<213> ORGANISM: Artificial
<220> FEATURE:
<223> OTHER INFORMATION: Primer

<400> SEQUENCE: 31
cgcagtccac cccagcttcc atatcacc                                          28

<210> SEQ ID NO 32
<211> LENGTH: 28
```

```
<212> TYPE: DNA
<213> ORGANISM: Artificial
<220> FEATURE:
<223> OTHER INFORMATION: Primer

<400> SEQUENCE: 32
cgcgctccac cccagcttcc atatcacc                                           28

<210> SEQ ID NO 33
<211> LENGTH: 28
<212> TYPE: DNA
<213> ORGANISM: Artificial
<220> FEATURE:
<223> OTHER INFORMATION: Primer

<400> SEQUENCE: 33
cgtattccac cccagcttcc atatcacc                                           28

<210> SEQ ID NO 34
<211> LENGTH: 28
<212> TYPE: DNA
<213> ORGANISM: Artificial
<220> FEATURE:
<223> OTHER INFORMATION: Primer

<400> SEQUENCE: 34
cgtcgtccac cccagcttcc atatcacc                                           28

<210> SEQ ID NO 35
<211> LENGTH: 28
<212> TYPE: DNA
<213> ORGANISM: Artificial
<220> FEATURE:
<223> OTHER INFORMATION: Primer

<400> SEQUENCE: 35
ctagttccac cccagcttcc atatcacc                                           28

<210> SEQ ID NO 36
<211> LENGTH: 28
<212> TYPE: DNA
<213> ORGANISM: Artificial
<220> FEATURE:
<223> OTHER INFORMATION: Primer

<400> SEQUENCE: 36
ctatgtccac cccagcttcc atatcacc                                           28

<210> SEQ ID NO 37
<211> LENGTH: 28
<212> TYPE: DNA
<213> ORGANISM: Artificial
<220> FEATURE:
<223> OTHER INFORMATION: Primer

<400> SEQUENCE: 37
ctcattccac cccagcttcc atatcacc                                           28

<210> SEQ ID NO 38
<211> LENGTH: 28
<212> TYPE: DNA
<213> ORGANISM: Artificial
<220> FEATURE:
<223> OTHER INFORMATION: Primer

<400> SEQUENCE: 38
ctgagtccac cccagcttcc atatcacc                                           28
```

<210> SEQ ID NO 39
<211> LENGTH: 28
<212> TYPE: DNA
<213> ORGANISM: Artificial
<220> FEATURE:
<223> OTHER INFORMATION: Primer

<400> SEQUENCE: 39
ctgcttccac cccagcttcc atatcacc            28

<210> SEQ ID NO 40
<211> LENGTH: 28
<212> TYPE: DNA
<213> ORGANISM: Artificial
<220> FEATURE:
<223> OTHER INFORMATION: Primer

<400> SEQUENCE: 40
tatcgtccac cccagcttcc atatcacc            28

<210> SEQ ID NO 41
<211> LENGTH: 28
<212> TYPE: DNA
<213> ORGANISM: Artificial
<220> FEATURE:
<223> OTHER INFORMATION: Primer

<400> SEQUENCE: 41
tagtctccac cccagcttcc atatcacc            28

<210> SEQ ID NO 42
<211> LENGTH: 28
<212> TYPE: DNA
<213> ORGANISM: Artificial
<220> FEATURE:
<223> OTHER INFORMATION: Primer

<400> SEQUENCE: 42
tatactccac cccagcttcc atatcacc            28

<210> SEQ ID NO 43
<211> LENGTH: 28
<212> TYPE: DNA
<213> ORGANISM: Artificial
<220> FEATURE:
<223> OTHER INFORMATION: Primer

<400> SEQUENCE: 43
tacattccac cccagcttcc atatcacc            28

<210> SEQ ID NO 44
<211> LENGTH: 28
<212> TYPE: DNA
<213> ORGANISM: Artificial
<220> FEATURE:
<223> OTHER INFORMATION: Primer

<400> SEQUENCE: 44
tacgctccac cccagcttcc atatcacc            28

<210> SEQ ID NO 45
<211> LENGTH: 28
<212> TYPE: DNA
<213> ORGANISM: Artificial
<220> FEATURE:
<223> OTHER INFORMATION: Primer

<400> SEQUENCE: 45
tagagtccac cccagcttcc atatcacc                                      28

<210> SEQ ID NO 46
<211> LENGTH: 28
<212> TYPE: DNA
<213> ORGANISM: Artificial
<220> FEATURE:
<223> OTHER INFORMATION: Primer

<400> SEQUENCE: 46
tagcttccac cccagcttcc atatcacc                                      28

<210> SEQ ID NO 47
<211> LENGTH: 28
<212> TYPE: DNA
<213> ORGANISM: Artificial
<220> FEATURE:
<223> OTHER INFORMATION: Primer

<400> SEQUENCE: 47
acacgtcatt caggttgggt gcaacagc                                      28

<210> SEQ ID NO 48
<211> LENGTH: 28
<212> TYPE: DNA
<213> ORGANISM: Artificial
<220> FEATURE:
<223> OTHER INFORMATION: Primer

<400> SEQUENCE: 48
acatctcatt caggttgggt gcaacagc                                      28

<210> SEQ ID NO 49
<211> LENGTH: 28
<212> TYPE: DNA
<213> ORGANISM: Artificial
<220> FEATURE:
<223> OTHER INFORMATION: Primer

<400> SEQUENCE: 49
acgactcatt caggttgggt gcaacagc                                      28

<210> SEQ ID NO 50
<211> LENGTH: 28
<212> TYPE: DNA
<213> ORGANISM: Artificial
<220> FEATURE:
<223> OTHER INFORMATION: Primer

<400> SEQUENCE: 50
acgcttcatt caggttgggt gcaacagc                                      28

<210> SEQ ID NO 51
<211> LENGTH: 28
<212> TYPE: DNA
<213> ORGANISM: Artificial
<220> FEATURE:
<223> OTHER INFORMATION: Primer

<400> SEQUENCE: 51
actgctcatt caggttgggt gcaacagc                                      28

<210> SEQ ID NO 52
<211> LENGTH: 28

```
<212> TYPE: DNA
<213> ORGANISM: Artificial
<220> FEATURE:
<223> OTHER INFORMATION: Primer

<400> SEQUENCE: 52
agagctcatt caggttgggt gcaacagc                                   28

<210> SEQ ID NO 53
<211> LENGTH: 28
<212> TYPE: DNA
<213> ORGANISM: Artificial
<220> FEATURE:
<223> OTHER INFORMATION: Primer

<400> SEQUENCE: 53
agatgtcatt caggttgggt gcaacagc                                   28

<210> SEQ ID NO 54
<211> LENGTH: 28
<212> TYPE: DNA
<213> ORGANISM: Artificial
<220> FEATURE:
<223> OTHER INFORMATION: Primer

<400> SEQUENCE: 54
agcattcatt caggttgggt gcaacagc                                   28

<210> SEQ ID NO 55
<211> LENGTH: 28
<212> TYPE: DNA
<213> ORGANISM: Artificial
<220> FEATURE:
<223> OTHER INFORMATION: Primer

<400> SEQUENCE: 55
agctctcatt caggttgggt gcaacagc                                   28

<210> SEQ ID NO 56
<211> LENGTH: 28
<212> TYPE: DNA
<213> ORGANISM: Artificial
<220> FEATURE:
<223> OTHER INFORMATION: Primer

<400> SEQUENCE: 56
agtagtcatt caggttgggt gcaacagc                                   28

<210> SEQ ID NO 57
<211> LENGTH: 28
<212> TYPE: DNA
<213> ORGANISM: Artificial
<220> FEATURE:
<223> OTHER INFORMATION: Primer

<400> SEQUENCE: 57
agtcttcatt caggttgggt gcaacagc                                   28

<210> SEQ ID NO 58
<211> LENGTH: 28
<212> TYPE: DNA
<213> ORGANISM: Artificial
<220> FEATURE:
<223> OTHER INFORMATION: Primer

<400> SEQUENCE: 58
atacttcatt caggttgggt gcaacagc                                   28
```

-continued

<210> SEQ ID NO 59
<211> LENGTH: 28
<212> TYPE: DNA
<213> ORGANISM: Artificial
<220> FEATURE:
<223> OTHER INFORMATION: Primer

<400> SEQUENCE: 59
atcagtcatt caggttgggt gcaacagc                28

<210> SEQ ID NO 60
<211> LENGTH: 28
<212> TYPE: DNA
<213> ORGANISM: Artificial
<220> FEATURE:
<223> OTHER INFORMATION: Primer

<400> SEQUENCE: 60
atcgttcatt caggttgggt gcaacagc                28

<210> SEQ ID NO 61
<211> LENGTH: 28
<212> TYPE: DNA
<213> ORGANISM: Artificial
<220> FEATURE:
<223> OTHER INFORMATION: Primer

<400> SEQUENCE: 61
atgattcatt caggttgggt gcaacagc                28

<210> SEQ ID NO 62
<211> LENGTH: 28
<212> TYPE: DNA
<213> ORGANISM: Artificial
<220> FEATURE:
<223> OTHER INFORMATION: Primer

<400> SEQUENCE: 62
atgtgtcatt caggttgggt gcaacagc                28

<210> SEQ ID NO 63
<211> LENGTH: 28
<212> TYPE: DNA
<213> ORGANISM: Artificial
<220> FEATURE:
<223> OTHER INFORMATION: Primer

<400> SEQUENCE: 63
cacgttcatt caggttgggt gcaacagc                28

<210> SEQ ID NO 64
<211> LENGTH: 28
<212> TYPE: DNA
<213> ORGANISM: Artificial
<220> FEATURE:
<223> OTHER INFORMATION: Primer

<400> SEQUENCE: 64
cactgtcatt caggttgggt gcaacagc                28

<210> SEQ ID NO 65
<211> LENGTH: 28
<212> TYPE: DNA
<213> ORGANISM: Artificial
<220> FEATURE:
<223> OTHER INFORMATION: Primer

```
<400> SEQUENCE: 65
cagattcatt caggttgggt gcaacagc                                    28

<210> SEQ ID NO 66
<211> LENGTH: 28
<212> TYPE: DNA
<213> ORGANISM: Artificial
<220> FEATURE:
<223> OTHER INFORMATION: Primer

<400> SEQUENCE: 66
cagcgtcatt caggttgggt gcaacagc                                    28

<210> SEQ ID NO 67
<211> LENGTH: 28
<212> TYPE: DNA
<213> ORGANISM: Artificial
<220> FEATURE:
<223> OTHER INFORMATION: Primer

<400> SEQUENCE: 67
catagtcatt caggttgggt gcaacagc                                    28

<210> SEQ ID NO 68
<211> LENGTH: 28
<212> TYPE: DNA
<213> ORGANISM: Artificial
<220> FEATURE:
<223> OTHER INFORMATION: Primer

<400> SEQUENCE: 68
catgctcatt caggttgggt gcaacagc                                    28

<210> SEQ ID NO 69
<211> LENGTH: 28
<212> TYPE: DNA
<213> ORGANISM: Artificial
<220> FEATURE:
<223> OTHER INFORMATION: Primer

<400> SEQUENCE: 69
cgacttcatt caggttgggt gcaacagc                                    28

<210> SEQ ID NO 70
<211> LENGTH: 28
<212> TYPE: DNA
<213> ORGANISM: Artificial
<220> FEATURE:
<223> OTHER INFORMATION: Primer

<400> SEQUENCE: 70
cgatctcatt caggttgggt gcaacagc                                    28

<210> SEQ ID NO 71
<211> LENGTH: 28
<212> TYPE: DNA
<213> ORGANISM: Artificial
<220> FEATURE:
<223> OTHER INFORMATION: Primer

<400> SEQUENCE: 71
cgcagtcatt caggttgggt gcaacagc                                    28

<210> SEQ ID NO 72
<211> LENGTH: 28
```

<212> TYPE: DNA
<213> ORGANISM: Artificial
<220> FEATURE:
<223> OTHER INFORMATION: Primer

<400> SEQUENCE: 72
cgcgctcatt caggttgggt gcaacagc					28

<210> SEQ ID NO 73
<211> LENGTH: 28
<212> TYPE: DNA
<213> ORGANISM: Artificial
<220> FEATURE:
<223> OTHER INFORMATION: Primer

<400> SEQUENCE: 73
cgtattcatt caggttgggt gcaacagc					28

<210> SEQ ID NO 74
<211> LENGTH: 28
<212> TYPE: DNA
<213> ORGANISM: Artificial
<220> FEATURE:
<223> OTHER INFORMATION: Primer

<400> SEQUENCE: 74
cgtcgtcatt caggttgggt gcaacagc					28

<210> SEQ ID NO 75
<211> LENGTH: 28
<212> TYPE: DNA
<213> ORGANISM: Artificial
<220> FEATURE:
<223> OTHER INFORMATION: Primer

<400> SEQUENCE: 75
ctagttcatt caggttgggt gcaacagc					28

<210> SEQ ID NO 76
<211> LENGTH: 28
<212> TYPE: DNA
<213> ORGANISM: Artificial
<220> FEATURE:
<223> OTHER INFORMATION: Primer

<400> SEQUENCE: 76
ctatgtcatt caggttgggt gcaacagc					28

<210> SEQ ID NO 77
<211> LENGTH: 28
<212> TYPE: DNA
<213> ORGANISM: Artificial
<220> FEATURE:
<223> OTHER INFORMATION: Primer

<400> SEQUENCE: 77
ctcattcatt caggttgggt gcaacagc					28

<210> SEQ ID NO 78
<211> LENGTH: 28
<212> TYPE: DNA
<213> ORGANISM: Artificial
<220> FEATURE:
<223> OTHER INFORMATION: Primer

<400> SEQUENCE: 78
ctgagtcatt caggttgggt gcaacagc					28

<210> SEQ ID NO 79
<211> LENGTH: 28
<212> TYPE: DNA
<213> ORGANISM: Artificial
<220> FEATURE:
<223> OTHER INFORMATION: Primer

<400> SEQUENCE: 79
ctgcttcatt caggttgggt gcaacagc    28

<210> SEQ ID NO 80
<211> LENGTH: 28
<212> TYPE: DNA
<213> ORGANISM: Artificial
<220> FEATURE:
<223> OTHER INFORMATION: Primer

<400> SEQUENCE: 80
tatcgtcatt caggttgggt gcaacagc    28

<210> SEQ ID NO 81
<211> LENGTH: 28
<212> TYPE: DNA
<213> ORGANISM: Artificial
<220> FEATURE:
<223> OTHER INFORMATION: Primer

<400> SEQUENCE: 81
tagtctcatt caggttgggt gcaacagc    28

<210> SEQ ID NO 82
<211> LENGTH: 28
<212> TYPE: DNA
<213> ORGANISM: Artificial
<220> FEATURE:
<223> OTHER INFORMATION: Primer

<400> SEQUENCE: 82
tatactcatt caggttgggt gcaacagc    28

<210> SEQ ID NO 83
<211> LENGTH: 28
<212> TYPE: DNA
<213> ORGANISM: Artificial
<220> FEATURE:
<223> OTHER INFORMATION: Primer

<400> SEQUENCE: 83
tacattcatt caggttgggt gcaacagc    28

<210> SEQ ID NO 84
<211> LENGTH: 28
<212> TYPE: DNA
<213> ORGANISM: Artificial
<220> FEATURE:
<223> OTHER INFORMATION: Primer

<400> SEQUENCE: 84
tacgctcatt caggttgggt gcaacagc    28

<210> SEQ ID NO 85
<211> LENGTH: 28
<212> TYPE: DNA
<213> ORGANISM: Artificial
<220> FEATURE:
<223> OTHER INFORMATION: Primer

```
<400> SEQUENCE: 85
tagagtcatt caggttgggt gcaacagc                                          28

<210> SEQ ID NO 86
<211> LENGTH: 28
<212> TYPE: DNA
<213> ORGANISM: Artificial
<220> FEATURE:
<223> OTHER INFORMATION: Primer

<400> SEQUENCE: 86
tagcttcatt caggttgggt gcaacagc                                          28
```